US006692951B2

(12) United States Patent
Quax et al.

(10) Patent No.: US 6,692,951 B2
(45) Date of Patent: *Feb. 17, 2004

(54) SECRETION FACTORS FOR GRAM-POSITIVE MICOORGANISMS, GENES ENCODING THEM AND METHODS OF USING IT

(75) Inventors: Wilhelmus J. Quax, Voorschoten (NL); Richard Kerkman, Zandvoort (NL); Cornelis P. Broekhuizen, Rijswijk (NL)

(73) Assignee: Genencor International, Inc., Palo Alto, CA (US)

( * ) Notice: Subject to any disclaimer, the term of this patent is extended or adjusted under 35 U.S.C. 154(b) by 25 days.

This patent is subject to a terminal disclaimer.

(21) Appl. No.: 10/147,936

(22) Filed: May 17, 2002

(65) Prior Publication Data

US 2003/0077729 A1 Apr. 24, 2003

Related U.S. Application Data

(62) Division of application No. 08/981,527, filed as application No. PCT/NL96/00278 on Jul. 5, 1996, now Pat. No. 6,410,262.

(30) Foreign Application Priority Data

Jul. 7, 1995 (EP) .............................. 95201871

(51) Int. Cl.[7] .......................... C12N 1/21; C12N 15/31; C07M 21/04
(52) U.S. Cl. .............................. 435/252.31; 435/252.3; 435/320.1; 536/23.7
(58) Field of Search ...................... 536/23.7; 435/252.3, 435/252.31, 320.1

(56) References Cited

PUBLICATIONS

**Ausubel, et al., *Current Protocols in Molecular Biology*, John Wiley and Sons, Inc., New York (1987).
Bernstein, Harris D. et al., <<Model for signal sequence recognition from amino–acid sequence of 54K subunit of signal recognition particle,>>*Nature*, vol. 340, pp. 482–486 (1989).
*Gilmore, Reid, "Protein Translocation across the Endoplasmic Reticulum: A Tunnel with Toll Booths at Entry and Exit," *Cell*, vol.75, pp. 589–592, Nov. 19, 1993.
Hann, Byron C. et al., <<Saccharomyces cerevisiae and Schizosaccharomyces pombe Contain a Homologue to the 54–kD Subunit of The Signal Recognition Particle That in *S. cerevisiae* is Essential for Growth,>>*The Journal of Cell Biology*, vol. 109, No. 6, pt. 2, pp. 3223–3230 (1989).
Hartl, Franz–Ulrich et al., <<The Binding Cascade of SecB to SecA to SecY/E Mediates Preprotein Targeting to the *E. coli* Plasma Membrane, >>*Cell*, vol. 63, pp. 269–279 (1990).

*Honda et al., "Cloning and characterization of a *Bacillus subtilis* gene encoding a homolog of the 54–kilodalton subunit of mammalian signal recognition particle and *Escherichia coli* Ffh," *J. Bacteriol*, vol. 175, pp. 4885–4894 (1993).
Jeong, Sang Min et al., <<Isolation and characterization of the secE homologue gene of *Bacillus subtilis*,>>*Molecular Microbiology*, vol. 10, No. 1, pp. 133–142 (1993).
Kumamoto, Carol A. et al., <<Evidence for Specificity at an Early Step in Protein Export in *Escherichia coli*,>>*Journal of Bacteriology*, vol. 163, No. 1, pp. 267–274 (1985).
Kumamoto, Carol A. et al., <<Mutations in a New Gene, secB, Cause Defective Protein Localization in *Escherichia coli*,>>*Journal of Bacteriology*, vol. 154, No. 1, pp. 253–260 (1983).
Luirink, Joen et al., <<Signal–sequence recognition by an *Escherichia coli* ribonucleoprotein complex,>>*Nature*, vol. 359, pp. 741–743, (1992).
*Luirink et al., "An alternative protein targeting pathway in Escherichia coli: studies on the role of Ftsy," *EMBO J*, pp. 2289–2296 (1994).
*Miller et al., "Interaction of *E. coli* Ffh/4.5S ribonucleoprotein and Ftsy mimics that of mammalian signal recognition particle and its receptor," *Nature*, pp. 657–659 (1994).
Nakamura, Kouji et al., <<Small Cytoplasmic RNA of *Bacillus subtilis*: Functional Relationship with Human Signal Recognition Particle 7S RNA and *Escherichia coli* 4.5S RNA, *Journal of Bacteriology*, vol. 174, No. 7, pp. 2185–2192 (1992).
*Oguro et al., "srb : a *Bacillus subtilis* gene encoding a homologue of the alpha–subunit of the mammalian signal recognition particle receptor," *DNA RES*, pp. 95–100 (1995).
Oliver, Donald B. et al., <<*E. coli* Mutant Oleiotropically Defective in the Export of Secreted Proteins,>>*Cell*, vol. 25, pp. 765–772 (1981).
Poritz, Mark A., et al., <<Human SRP RNA and *E. coli* 4.5S RNA Contain a Highly Homologous Structural Domain, >>*Cell*, vol. 55, pp. 4–6 (1988).*Quax et al., "Correct secretion of heterologous protein from *Bacillus licheniformis*," *Industrial Microorganisms: Basic and Applied Molecular Genetics*, pp. 143–147 (1993).

(List continued on next page.)

Primary Examiner—Elizabeth Slobodyansky
(74) Attorney, Agent, or Firm—Genencor International, Inc.

(57) ABSTRACT

Heterologous protein secretion from Gram-positive bacteria, in particular from Bacilli has, with few exceptions, met with little success. Incompatibility of the heterologous proteins with the protein secretion machinery of the host is the main cause of this effect. This limiting factor for the production of heterologous proteins in commercially significant concentrations from *Bacillus subtilis* is removed by overexpressing the *Bacillus subtilis* protein FtsY or FtsY protein in combination with overexpression of other members of the bacterial signal recognition particle. Said gene(s) is(are) overexpressed in Bacillus host cells expressing a heterologous protein which then shows an increased amount of the heterologous protein secreted in the surrounding medium.

12 Claims, 13 Drawing Sheets

OTHER PUBLICATIONS

*Ribes, U. et al., "*E. coli* 4.5S RNA Is Part of a Ribonucleoprotein particle That Has Properties Related to Signal Recognition Particle," *Cell*, V. 63, pp.591–600, Nov. 2, 1990.

Romisch, Karin et al., <<Homology of 54K protein of signal–recognition particle, docking protein and two *E. coli* proteins with putative GTP–binding domains,>>*Nature*, vol. 340, pp. 478–482. (1989).

Sadaie, Yoshito et al., <<Sequencing revels similarity of the wild–type div+ gene of *Bacillus subtilis* to the *Escherichia coli* secA gene,>>*Gene*, vol. 98, pp. 101–105 (1991).

Samuelsson, Tore, <<A Mycoplasma protein homologous to mammalian SRP54 recognizes a highly conserved domain of SRP RNA, >>*Nucleic Acids Research*, vol. 20, No. 21, pp. 5763–5770 (1992).

Schiebel, Elmar et al., <<▲$u_H$+and ATP Function at Different Steps of the Catalytic Cycle of Preprotein Translocase, >>*Cell*, vol. 64, pp. 927–939 (1991).

*Struck et al., "Transcription and processing of *Bacillus subtilis* small sytoplasmic RNA," *Mol. Gen. Genet.*, 215, 478–482, 1989.

Struck, Joachim C.R., et al., <<Phylogenetic and biochemical evidence for a secondary structure model of a small cytoplasmic RNA from Bacilli,>>*Eur. J. Biochem.*, vol. 192, pp. 17–24 (1990).

Suh, J.W. et al, <<Isolation of a secY homologue from *Bacillus subtilis* : evidence for a common protein export pathway in eubacteria, >>*Molecular Microbiology*, vol. 4, No. 2, pp.305–314 (1990).

Ullu, Elisabetta et al, <<Human genes and pseudogenes for the 7SL RNA component of signal recognition particle, >>*EMBO Journal*, vol. 3, No. 13, pp. 3303–3310 (1984).

Van der Vossen, Jos M.B.M. et al, <<Isolation and Characterization of *Streptococcus cremoris* Wg2–Specific Promoters,>>*Applied and Environmental Microbiology*, vol. 53, No. 10, pp. 2452–2457 (1987).

Van Dijl, Jan Maarten et al, <<Signal peptidase I of *Bacillus subtilis* : patterns of conserved amino acids in prokaryotic and eukaryotic type I signal peptidases, >>*The EMBO Journal*, vol. 11, No. 8, pp. 2819–2828 (1992).

Yansura, Daniel G. et al., <<Use of the *Escherichia coli* lac repressor and operator to control gene expression in *Bacillus subtilis*, >>*Proc. Natl. Acad. Sci. USA*, vol. 81, pp. 439–443 (1984).

*Wolin, <<From the elephant to *E. coli* : SRP–dependent protein targeting,>>*Cell*, pp. 787–790 (1994).

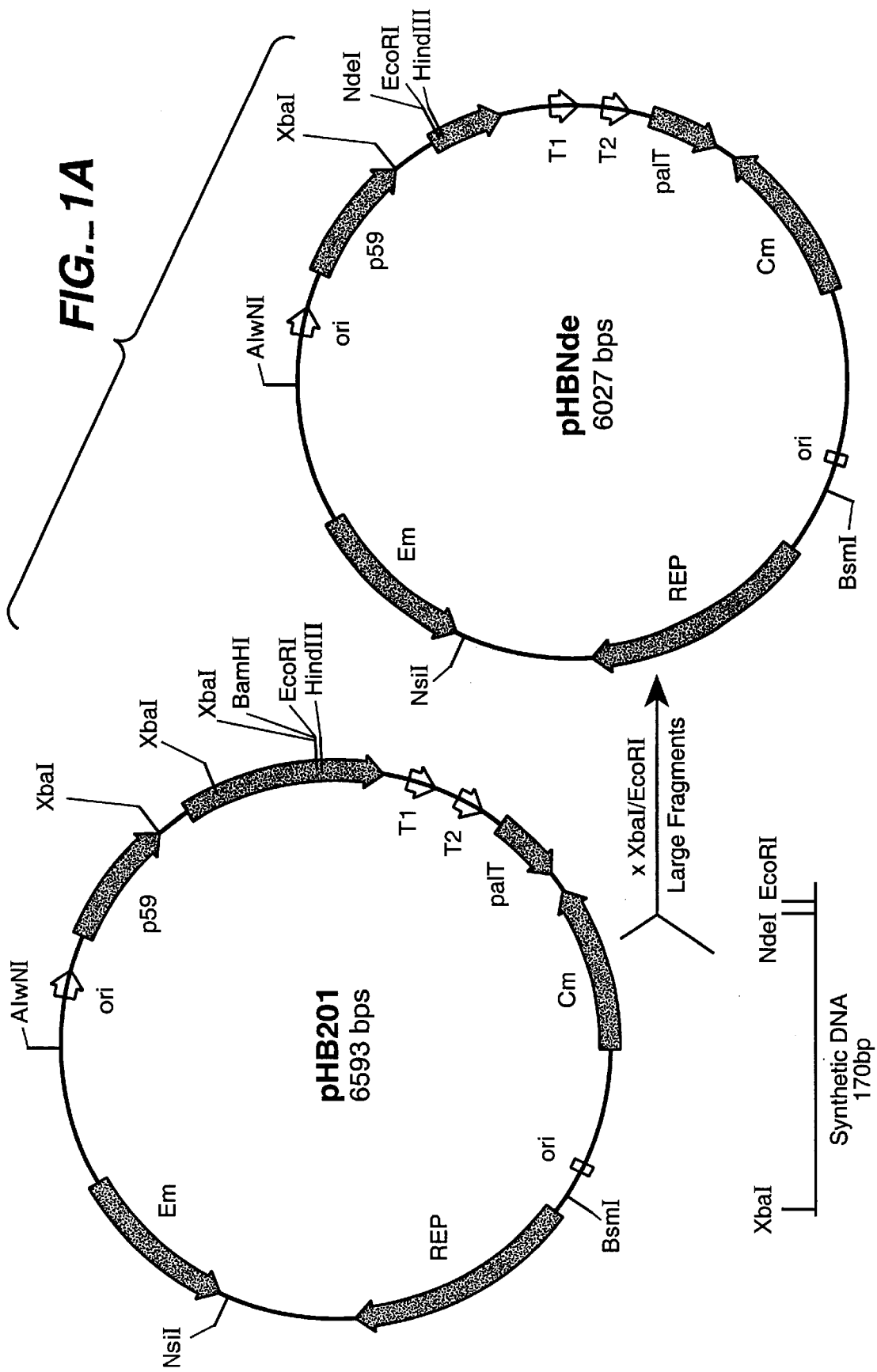
FIG._1A

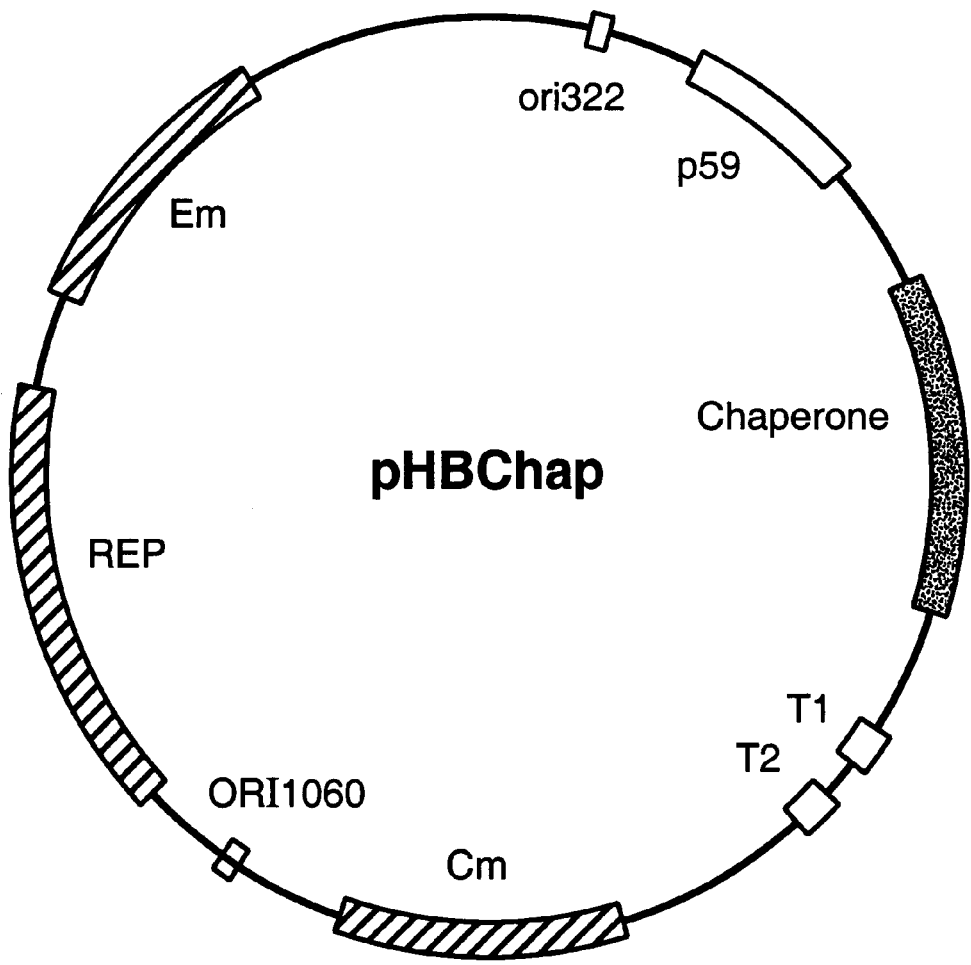
FIG._1B

I

| | | | | |
|---|---|---|---|---|
| SRα_CANFA | PYVVTFC | GVNGVGK | STNLAKISFWLLENGFSVLIAACDTFRAGAVEHVRTHTR | 467 |
| SRα_HUMAN | PYVVTFC | GVNGVGK | STNLAKISFWLLENGFSVLIAACDTFRAGAVEQLRTHTR | 467 |
| FTSY_YEAST | PYVFSIV | GVNGVGK | STNLSKLAFWLLQNNFKVLIVACDTFRSGAVEQLRVHVE | 449 |
| DOCK_SULSO | PFVIIFF | GVNGVGK | TTTIAKVVNMLKKNNLSTIIAASDTFRAAAQEQLAYHAS | 225 |
| FTSY_ECOLI | PFVILMV | GVNGVGK | TTTIGKLARQFEQQGKSVMLAAGDTFRAAAVEQLQVWGQ | 345 |

5' ━━━ 3'
     PR1

| | | |
|---|---|---|
| SRα_CANFA | RLSALH------PPEKHA--GPTMVQLFEKGYGKDA--AGIAMEAIAFARNQGF | 514 |
| SRα_HUMAN | RLSALH------PPEKHG--GRTMVQLFEKGYGKDA--AGIAMEAIAFARNQGF | 514 |
| FTSY_YEAST | NLAQLMDDSHVRGSKNKRGKTGNDYVELFEAGYGGSDLVTKIAKQAIKYARDQNF | 569 |
| DOCK_SULSO | KLE----------------------VQLIRGKYGADP--ASVAFDAISFAKSRNI | 319 |
| FTSY_ECOLI | RNN----------------------IPVIAQHTGADS--ASVIFDAIQAAKARNI | 445 |

3' ━━━ 5'
     PR3

II

| | | | | |
|---|---|---|---|---|
| SRα_CANFA | DVVLV | DTAG | RMQDNAPLMTAL | 535 |
| SRα_HUMAN | DVVLV | DTAG | RMQDNAPLMTAL | 535 |
| FTSY_YEAST | DIVLM | DTAG | RRHNDPTLMSPL | 590 |
| DOCK_SULSO | DVVLI | DTAG | RMHIDSDLVEEL | 340 |
| FTSY_ECOLI | DVLIA | DTAG | RLQNKSHLMEEL | 466 |

```
SRα _CANFA    STNLAKISFWLLENGFSVLIAAC    454
SRα _HUMAN    STNLAKISFWLLENGFSVLIAAC    454
FTSY_YEAST    STNLSKLAFWLLQNNFKVLIVAC    433
DOCK_SULSO    TTTIAKVVNMLKKNNLSTIIAAS    209
FTSY_ECOLI    TTTIGKLARQFEQQGKSVMLAAG    329
              .*...*.  . ...  .....*
FTSY_BSUB     TTTIGKLAHKMKQEGKSVVLAAG

Identity   :  3 (13.0%)
Similarity : 14 (60.9%)
```

FIG._2B

* MOLECULE FEATURES *

| Type | Start | End | Compl | Name | Description |
|---|---|---|---|---|---|
| GENE | 1 | 2286 | | 'orf2 | 'orf2 = 3' part of ORF showing homology to DNA segregation genes like Yeast SMC1. |
| GENE | 2306 | 3295 | | FtsY | FtsY |
| REGION | 3294 | 3329 | | T | Terminator |
| GENE | 3673 | 3332 | (C) | orf3 | orf3 |
| REGION | 3904 | 3939 | | P | promoter orfz-ffh operon |
| GENE | 3992 | 4324 | | orf1 | orf1 |
| GENE | 4338 | 4370 | | ffh' | ffh' = 5' part of ffh gene |

NAME:      FTSY_BACSU_TO           4370 BPS DNA
                    *  *  *   S E Q U E N C E   *  *  *

```
   1 CTGCAGGAAC GGCATGATAT TTCTGCGCGT AAAGCCGCAT GTGAAACGGA ATTTGCCCGA
  61 ATTGAGCAGG AGATTCACAG TCAAGTCGGT GCATATCGTG ATATGCAGAC AAAATATGAG
 121 CAGAAAAAGC GCCAATACGA AAAAAATGAA TCCGCTCTGT ATCAGGCATA CCAATACGTT
 181 CAGCAAGCGA GATCAAAAAA GGACATGCTT GAGACGATGC AGGGAGATTT CTCCGGCTTT
 241 TATCAAGGTG TTAAAGAAGT GCTGAAAGCG AAAGAGCGCC TTGGCGGAAT TCGCGGAGCG
 301 GTTCTTGAGC TGATTTCTAC AGAACAGAAG TATGAAACGG CCATTGAAAT AGCGCTCGGC
 361 GCTTCTGCTC AACACGTCGT GACCGACGAT GAACAATCTG CCCGCAAAGC GATTCAATAT
 421 TTAAAGCAGA ATTCCTTCGG CCGGGCGACG TTTCTGCCTC TTTCTGTTAT TAGAGACCGC
 481 CAGCTTCAAA GCCGTGACGC GGAAACAGCC GCCCGGCATT CATCATTTCT CGGGGTTGCC
 541 AGTGAACTTG TCACATTTGA TCCTGCGTAT CGAAGCGTCA TCCAGAATCT TCTTGGAACC
 601 GTTCTGATCA CAGAGGACTT AAAGGGTGCA AACGAGCTTG CGAAGCTTCT CGGGCACCGG
 661 TACCGCATCG TAACCCTTGA GGGAGATGTT GTGAACCCCG GTGGTTCAAT GACGGGCGGC
 721 GCGGTTAAAA AGAAAAATAA CTCCCTCCTT GGAAGAAGCC GGGAGCTAGA AGATGTGACG
 781 AAACGGCTCG CTGAAATGGA AGAGAAAACG GCACTGCTTG AACAAGAGGT CAAAACCCTT
 841 AAGCACTCCA TTCAGGATAT GGAGAAAAAA CTGGCTGACT TAAGAGAAAC CGGGGAAGGC
```

FIG._3A

```
 901  TTAAGGTTAA AGCAGCAGGA TGTGAAAGGC CAGCTGTACG AACTTCAAGT TGCCGAGAAA
 961  AATATCAATA CCCATTTAGA GCTCTATGAT CAAGAAAAAT CTGCTCTGTC AGAAAGCGAT
1021  GAAGAGAGAA AAGTGCGCAA ACGCAAGCTT GAAGAAGAGC TCTCTGCCGT ATCTGAAAAG
1081  ATGAAACAGC TTGAAGAGGA CATAGACAGA CTGACAAAAC AAAAACAAAC GCAATCCTCA
1141  ACGAAAGAGT CTCTCTCCAA CGAGCTGACT GAGCTGAAGA TCGCAGCGGC CAAAAAAGAG
1201  CAGGCTTGCG AGGGGGAAGA GGACAACCTT GCCAGATTAA AGAAAGAGCT CACTGAAACA
1261  GAGCTTGCGT TAAAAGAAGC AAAAGAAGAC TTAAGCTTCT TAACGTCAGA GATGTCATCT
1321  AGCACCAGCG GCGAAGAAAA GCTGGAAGAA GCAGCAAAAC ATAAATTGAA TGACAAAACG
1381  AAAACGATCG AACTGATTGC ATTAAGGCGC GATCAGCGCA TCAAGCTTCA GCATGGGCTT
1441  GATACGTATG AGCGTGAGCT GAAAGAAATG AAACGCCTGT ATAAACAAAA AACAACGCTC
1501  TTAAAAGACG AAGAAGTCAA ACTTGGACGA ATGGAAGTCG AGCTTGATAA TTTACTCCAA
1561  TACTTACGGG AGGAATACAG CTTGTCCTTT GAGGGGGCAA AAGAGAAATA TCAGCTTGAA
1621  ACTGATCCAG AGGAAGCCAG AAAGCGCGTG AAGCTGATTA AACTCGCAAT TGAAGAGCTG
1681  GGTACCGTGA ACCTCGGAAG CATAGATGAG TTTGAGAGGG TCAACGAACG GTACAAGTTT
1741  CTGTCGGAAC AAAAAGAAGA TTTAACAGAA GCGAAAAATA CCTTGTTCCA AGTGATTGAA
1801  GAAATGGATG AAGAAATGAC GAAGCGCTTT AACGACACAT TCGTCCAAAT CCGCTCACAC
1861  TTTGATCAAG TTTTCCGCTC CTTATTCGGA GGAGGGCGAG CTGAACTGAG GCTCACCGAT
1921  CCTAACGACT CCTCATCAGG ATCGAGATTA TCGCTCAGCC GCCGGGGAAA AACTCCAAAC
1981  TTTAACCTCC TGTCAGGCGG AGAGCGTGCG CTTACTGCTA TAGCGCTCTT ATTCTCAATC
2041  CTAAAGGTTC GTCCAGTGCC GTTTTGCGCC CTTGACGAAG TAGAGGCTGC GCTCGACGAA
2101  GCGAATGTGT TCCGATTTGC GCAGTACTTA AAAAAATACA GCAGCGATAC TCAGTTTATT
2161  GTGATTACCC ACAGAAAAGG AACGATGGAG GAAGCGGATG TGCTTTATGG CGTAACCATG
2221  CAGGAATCCG GTGTTTCCAA GGTAATTTCA GTTAAGCTGG AAGAAACAAA AGAATTCGTT
2281  CAGTAACGAG GAAAGAGGTT AAAAGATGAG CTTTTTAAA AAATTAAAAG AGAAAATCAC
2341  AAAACAGACA GATTCCGTAT CTGAAAAGTT TAAGGATGGC CTTGAAAAAA CAAGAAACTC
```

*FIG._3B*

```
2401  CTTTCAAAAC AAAGTGAATG ATCTTGTATC CCGTTACCGT AAAGTGGATG AGGATTTCTT
2461  CGAAGAGCTT GAAGAGGTTC TTATCAGCGC GGATGTCGGT TTTACAACCG TTATGGAATT
2521  AATAGATGAG CTGAAAAAAG AAGTCAAACG CAGAAATATT CAAGATCCAA AGGAAGTCAA
2581  GTCAGTGATT TCTGAGAAAC TGGTCGAGAT TTATAACAGC GGAGATGAGC AAATTTCAGA
2641  ACTGAACATC CAGGATGGGC GTTTAAACGT AATCCTTCTG GTAGGTGTAA ACGGCGTCGG
2701  GAAAACAACA ACGATCGGAA AGCTTGCTCA TAAAATGAAA CAAGAAGGAA AATCTGTTGT
2761  ACTTGCCGCC GGAGACACTT TTAGAGCGGG AGCCATTGAA CAGCTGGAAG TATGGGGAGA
2821  GCGTACAGGA GTGCCTGTCA TTAAGCAGAC GGCAGGAAGC GATCCGGCGG CTGTCATCTA
2881  CGATGCTGTT CATGCTGCGA AAGCAAGAAA TGCCGATGTA TTAATTTGTG ATACGGCAGG
2941  GCGTCTCCAA AACAAAGTAA ATCTCATGAA AGAGCTTGAA AAAGTAAAAC GTGTTATCGA
3001  AAGAGAAGTT CCTGAAGCTC CGCATGAGGT GCTGCTTGCC CTTGATGCCA CGACCGGCCA
3061  AAATGCAATG GCTCAGGCAA AAGAATTCTC TAAAGCAACA AATGTTACCG GCATTGCTTT
3121  AACGAAGCTT GACGGTACGG CAAAAGGCGG TATCGTCCTT GCGATTCGCA ACGAGCTTCA
3181  CATCCCGGTT AAACTAGTCG GTTTAGGAGA AAAAGTTGAT GACCTTCAGG AATTTGATCC
3241  AGAATCCTAT GTGTACGGAC TCTTTTCAGA TTTAGTGGAA AAAGCCGACG ATTAAGAAAA
3301  AGGCCCCAAC ATCTTGGGGC CTTTTTCTTT TTTATCTTCT TACTTGATAG GCGAAATGAT
3361  AAAGGCTGTT ATCAGTGGAT ACCAGTCTTG ACTCACCAGA AAAAACTCTG AATGGGATGA
3421  TGTCATAGTA ATGAACGGAA ACAGATGTGT AATACGTATA GTAACCAGCA GCTGGCCCCA
3481  AATACATTGG AACCTCAAAT GTTCCGTTTG CATCAGTCGT TCCTGAAGCA GTTTGTGTTG
3541  TGTTTCCGAC CTTCGTGTCC GCTTCAAATC TTACGGGCGC GTTTGGCACT GGCTGTCCGT
3601  TTTGGTCGAG TAATTTGCCG CTTACTGTAA TATTGTACTT GACTCGCAAT ATTGACCTTG
3661  TCCGTAATTG ATTTTACCGT ATACCCTCC ATCTGTGCTG ATATTTGTGA TTGAGGCCTT
3721  ATAAGGTGCC TCAGCAGCGT CTGCTTGCTG TGCCGGGAAA CCTATTGTAA ACAGGGCTGC
3781  CAGACATAAC ATAAACAATA AACCGATTTT TTTCATAAAA ATCCTCCTTA AAATAGGGTT
3841  CATATACAAT ATCGGAATAA ATTGGATGAT ATTTAGCGTA TTTTGGAAAA GTTAATCGCC
```

FIG._3C

```
3901  GCTTTGACAA GATAAAAACT TGACAGTGTC ATTAAAACCG TGTAAACTAA GTTATCGTAA

3961  AGGGATTTGA CTTAACAAGG GGAGAGCTCA AATGTCACTC GAAAAGACAA GCAGAATGAA

4021  TTATCTGTTT GATTTTTATC AGCCGTTGTT GACGTCAAAA CAGAAGAGCT ATATGTCGCT

4081  TTATTATTTG GACGATTTCT CCCTAGGCGA AATAGCCGAA GAATATGAGG TTTCAAGACA

4141  AGCTGTTTAT GATAACATCA AACGAACAGA AGCAATGCTT GAACAATATG AAGAAAAGCT

4201  GCTCCTTTTG AAAAGTTTC AGGAGCGTAA AGAGATGTTT AATAAGCTGA AGGAGCTTGC

4261  TTCCGGTTCA AAAGAAGAGG AAGAAATTAC AGCTCTGATT GAAGCGCTTG AGAAATTAGA

4321  TTAGGAGGCG GCAAACTATG GCATCTGAAG GATTAGCCGA CCGACTGCAG
```

FIG._3D

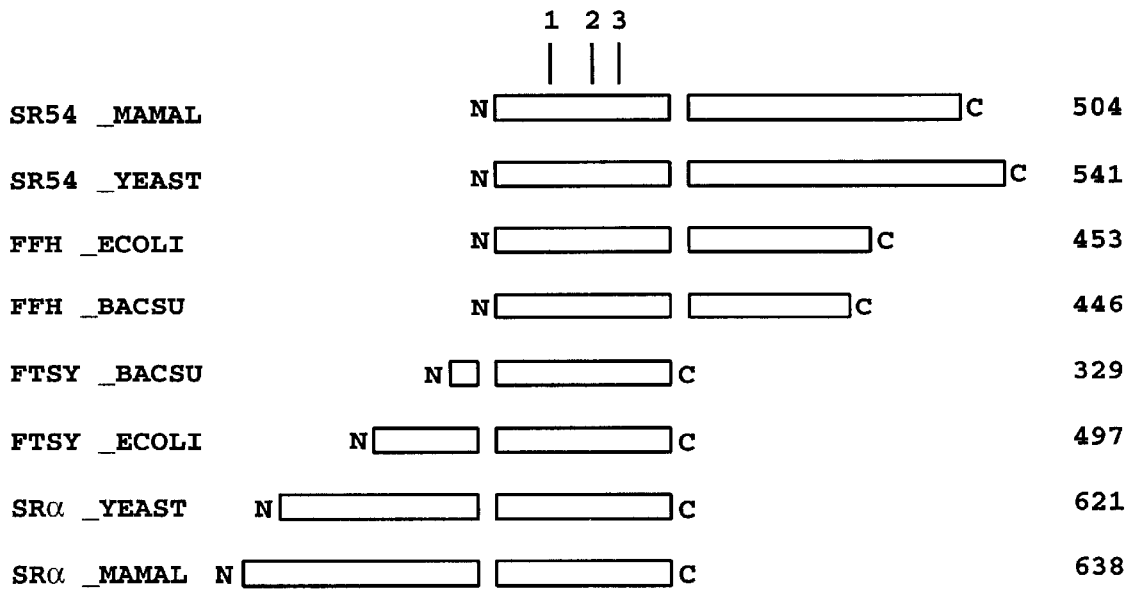

FIG._4

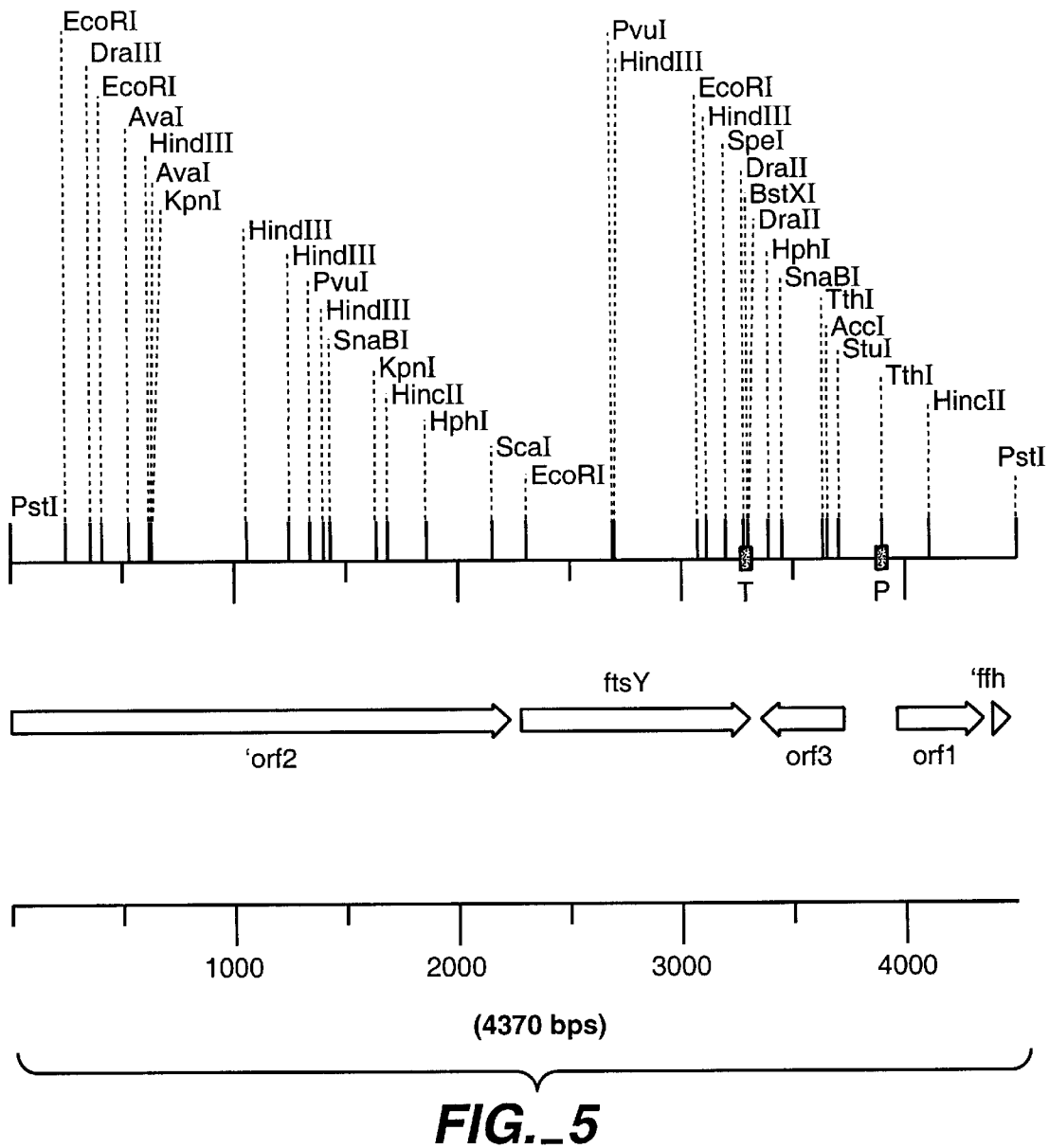
FIG._5

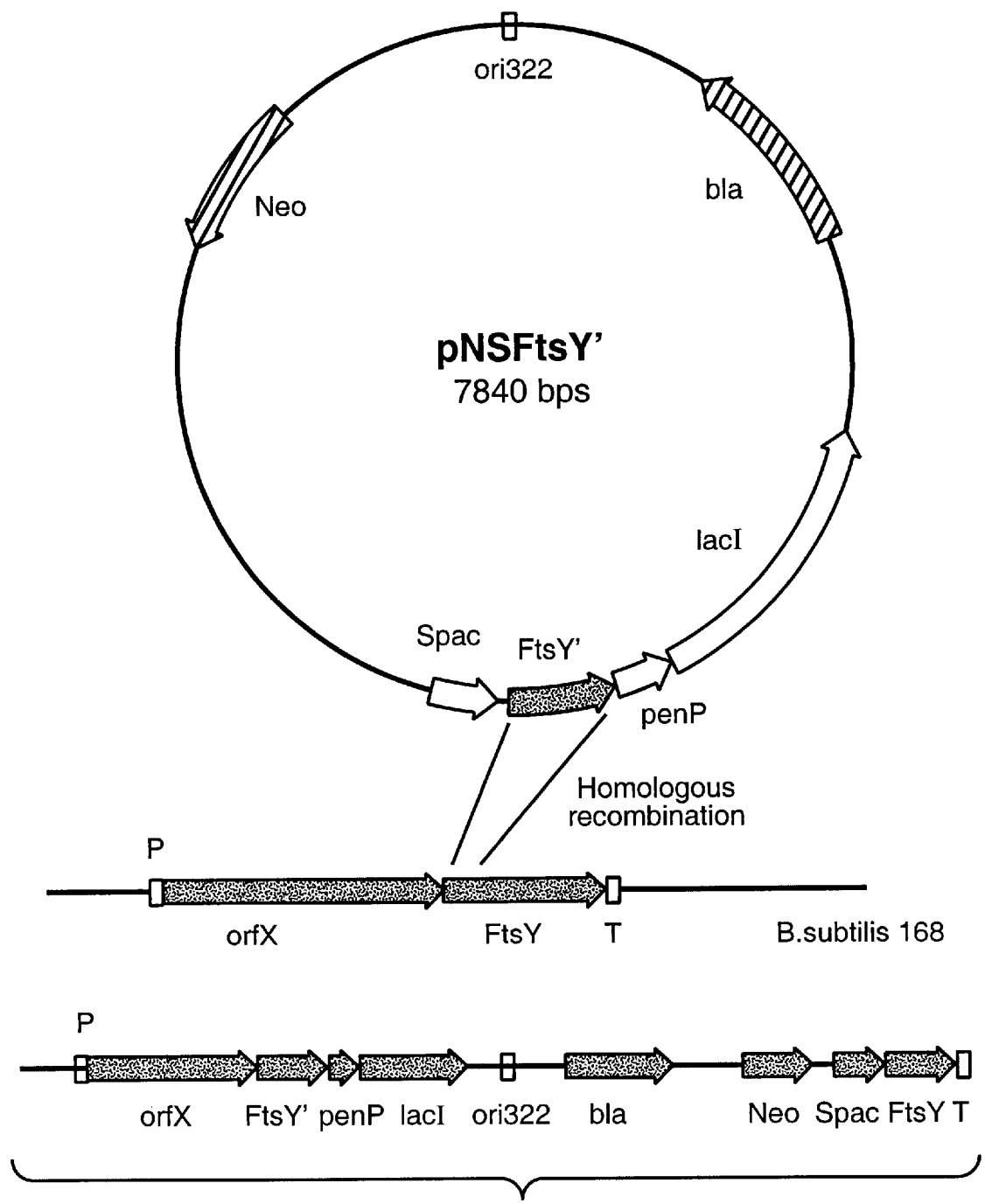
FIG._6

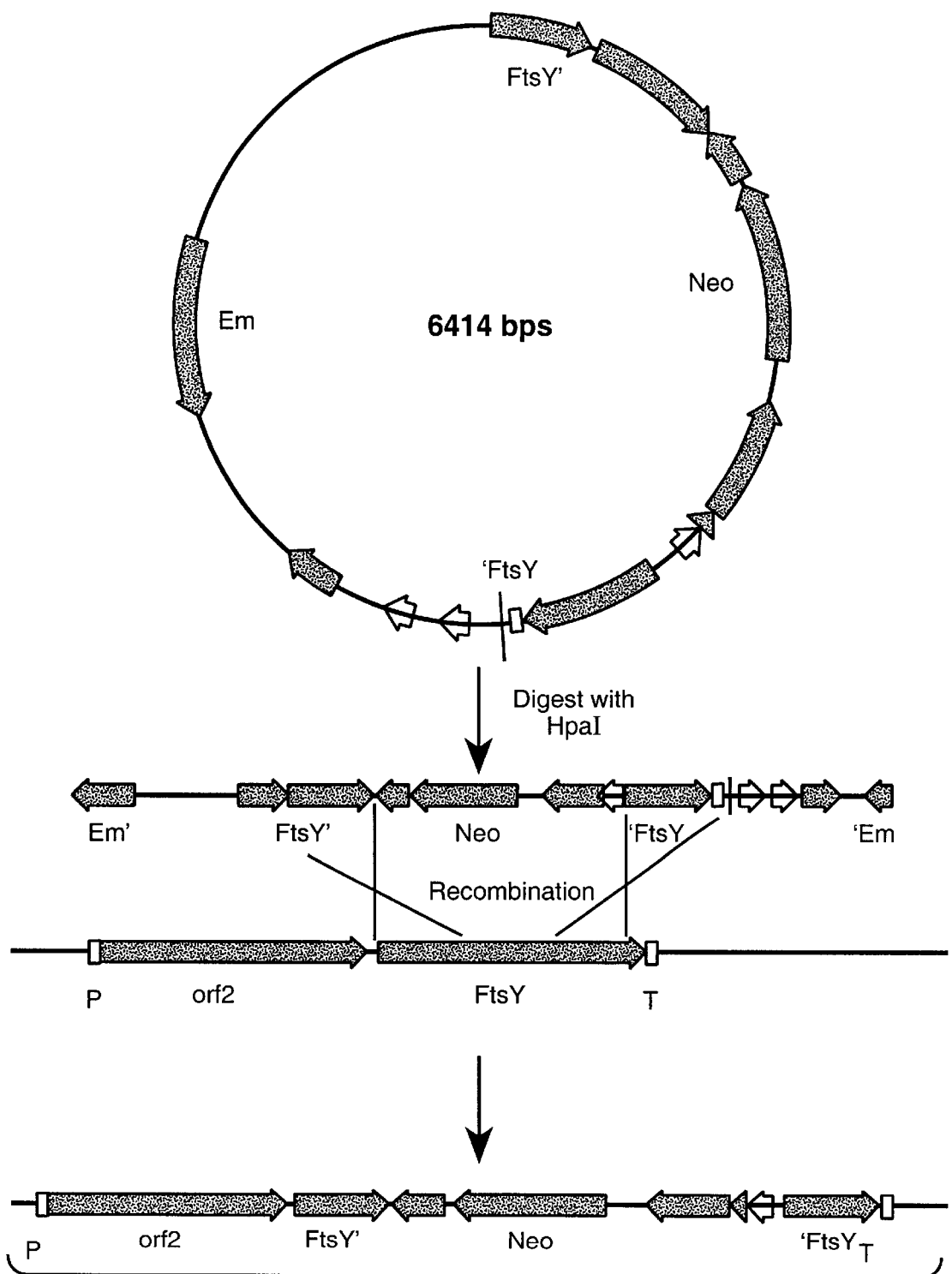
FIG._7

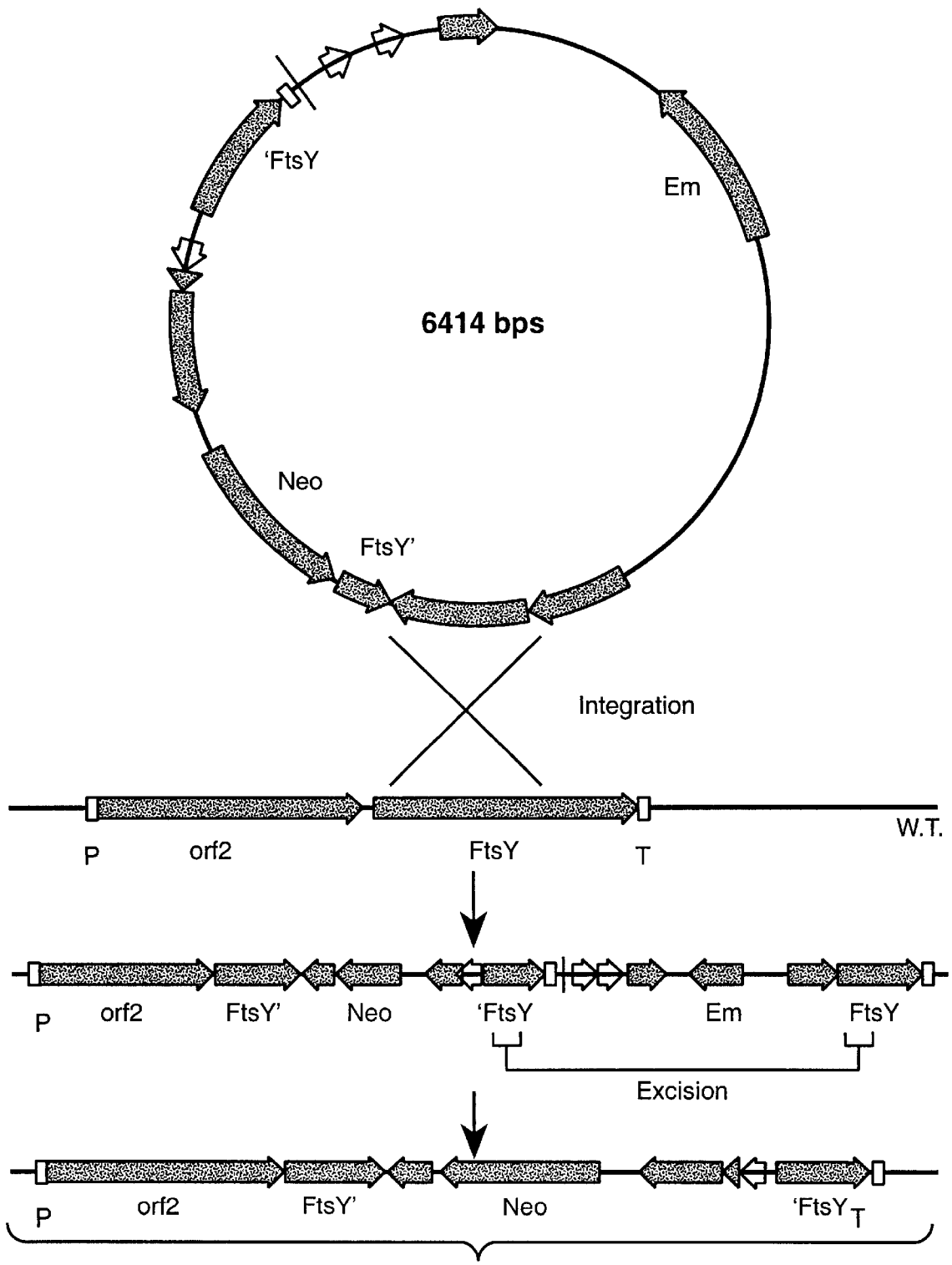
FIG._8

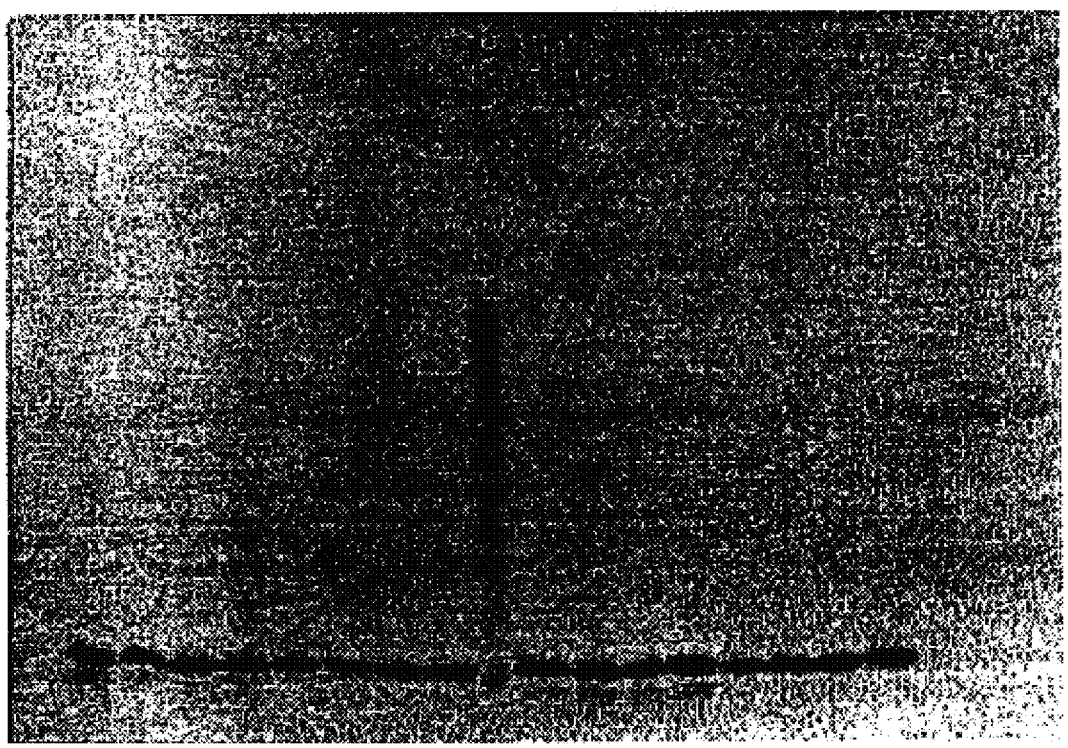
0" 15" 30" 60" 0" 15" 30" 60"    0" 15" 30" 60" 0" 15" 30" 60"
   pellet        sup            pellet        sup
FIG._9

SECRETION FACTORS FOR GRAM-POSITIVE MICOORGANISMS, GENES ENCODING THEM AND METHODS OF USING IT

This is a Divisional of U.S. patent application Ser. No. 08/981,527, filed Dec. 16, 1997, now U.S. Pat. No. 6,410,262, which is a 371 of PCT Application No. PCT/NL96/00278 filed Jul. 5, 1996 which claims priority European Patent Application No. 95201871.1 filed Jul. 7, 1995.

FIELD OF THE INVENTION

This invention relates to processes for the production of proteins by micro-organisms. Specifically, it relates to the secretion of heterologous proteins by micro-organisms, in particular by Gram-positive bacteria, especially by the bacterial host Bacillus.

It also relates to (the overexpression of) a novel gene encoding a protein involved in the early stages of prokaryotic protein secretion. Specifically, it relates to the overexpression of said gene within a Bacillus host (over)expressing heterologous proteins.

BACKGROUND OF THE INVENTION

B. subtilis and (closely) related bacilli secrete proteins directly into the growth medium to high concentrations. Secretion as a mode of production of proteins of interest, be it homologous to the host or heterologous to the host, be it of recombinant origin or not, provides several advantages over intracellular production. It for instance facilitates purification of the product, it theoretically will lead to a higher yield, no aggregation of the product will occur, and it gives the possibility for continuous cultivation and production. However, attempts to secrete heterologous proteins from B. subtilis and (closely) related organisms at commercially significant concentrations have, with few exceptions, met with little success.

Nearly all secreted proteins use an amino-terminal protein extension, known as the signalpeptide, which plays a crucial role in the targeting to, and translocation of precursor proteins across the membrane and which is proteolytically removed by a signalpeptidase during or immediately following membrane transfer. The newly synthesized precursor proteins are recognized by specific proteins in the cytoplasm collectively called chaperones. These chaperones prevent polypeptides, destined for translocation, to aggregate or fold prematurely leading to an export incompatible conformation.

For instance, SecB, GroEL/GroES and DnaK/DnaJ are the presently known chaperones in the export pathway of E. coli. For the productive binding of precursor proteins to translocation sites in the cytoplasmic membrane SecA is needed. SecA, a protein of which cytoplasmic, peripheral as well as integral membrane forms have been detected, has an ATPase activity which mediates the initial channelling of precursor proteins into the export pathway.

The SecA subunit acts as a receptor recognizing the leader and mature domains of the preproteins (Lill et al. 1990) as well as the SecB chaperone (Hartl et al. 1990). It has been suggested that SecA penetrates into the membrane, after binding of ATP, and so promotes the coinsertion of the preprotein. After hydrolysis of bound ATP the preprotein is released from the SecA protein (Schiebel et al. 1991). Translocation is completed with the proton motive force as the main driving force and requires members of the integral membrane part of the preprotein translocase complex like SecY, SecE and SecG (p12/Band1). SecD and SecF are also integral membrane proteins and are probably participating in the late steps of protein translocation.

For many years, the protein secretion machinery in prokaryotes has been considered to be independent from the protein secretion system found in higher eukaryotes (Luirink et al, 19920. In mammalians, targeting of secretory proteins to the endoplasmic reticulum (ER) is mediated by the signal recognition particle (SRP), which is a ribonucleoprotein particle composed of one RNA molecule (SRP 7S RNA) and six polypeptides of 9, 14, 19, 54, 68 and 72 kD. The SRP proteins are associated with the RNA as either monomers (SRP19 and SRP54) or heterodimers (SRP9/14 and SRP68/72).

As soon as the signal peptide of secreted and transmembrane proteins has emerged from the ribosome, it is recognized and bound by SRP, which also has affinity for the ribosome. This association slows down the elongation of the polypeptide chain (elongation arrest). When the complex of SRP, nascent polypeptide chain, and ribosome bind to the SRP receptor (SR or docking protein) associated with the ER membrane, the nascent polypeptide chain is displaced from SRP in a GTP-dependent reaction and protein translation is resumed.

The translocation of the polypeptide into the ER takes place co-translationally through a protein pore, the translocon (Gilmore et al. 1993). Thus, the SRP functions both as a cytosolic chaperone preventing premature folding of the preprotein by coupling translation to translocation and as a pilot to guide the preprotein to the SRP receptor complex in the membrane. The 54 kD subunit of SRP (SRP54) binds to the signal peptide when it emerges from the ribosome and therefore seems to have a key function in the SRP-mediated process of protein secretion.

To day more and more data become available indicating that an SRP-mediated export pathway may also function in other organisms. Homologues of mammalian SRP components have been isolated from Yeast (Hann et al. 1989), E. coli (Bernstein et al. 1989, and Rymisch et al. 1989), Mycoplasma mycoides (Samuelsson, 1992) and Bacillus subtilis (Struck et al. 1989, and Honda et al. 1993).

So it is likely that an SRP-mediated pathway functions in prokaryotes in a separate secretory pathway or may form part of the general secretory pathway.

In E. coli members of an SRP-like secretory pathway were identified. These members are Ffh (Fifty four homologue) and a 4.5S RNA molecule which are homologous to the SRP54 and SRP 7S RNA of eukaryotic SRP (Ribes et al. 1990). It is shown that Ffh interacts specifically with the signal sequence of nascent presecretory proteins (Luirink et al. 1992). E. coli protein FtsY, which originally has been implicated in cell division (because its gene is located in an operon together with FtsE and FtsX) displays striking sequence similarity with the subunit of mammalian docking protein. Several observations suggest that FtsY is the functional E. coli homologue of the mammalian SRP receptor (Luirink et al. 1994). Depletion of either FtsY, Ffh or the RNA component of the E. coli SRP affects the export of several secretory proteins.

Also in B. subtilis components of the SRP-like secretory pathway have been found. The Small Cytoplasmic RNA (scRNA) was shown to have a functional relationship with the human SRP 7S RNA and the E. coli 4.5S RNA (Nakamura et al., 1992). The B. subtilis scRNA is transcribed from the scr gene as a 354 nucleotide precursor which is then processed to a 271 nucleotide RNA at the 5' and 3' end (Struck et al., 1989), which is similar to its eukaryotic homologue (300 nucleotides) but much larger than the E. coli 4.5S RNA (114 nucleotides). Also the secundary structure of the scRNA is very similar to the eukaryotic SRP 7S RNA, lacking only the domain III (Struck and Erdmann, 1990). This is in contrast to the other eubacterial SRP-like RNAs, which only fold into a single hairpin corresponding to domain IV (Poritz et al., 1988). Therefore the B. subtilis scRNA is both in size and secundary structure an intermediate between prokaryotic and eukaryotic SRP-like RNA.

Besides the scr gene another gene encoding a SRP constituent has been isolated from B. subtilis. The ffh gene was found to encode the Ffh protein which shows homology to both the E. coli and eukaryotic SRP54 protein (Honda et al., 1993).

It is not unlikely that chaperones or members of the SRP-like secretion pathway may become a rate-limiting step in the secretion pathway, the result of which being that the majority of the heterologous protein expressed will aggregate or fold prematurely. This effect could be the reason why attempts to secrete heterologous proteins in high amounts from Gram-positive micro-organisms, in particular B. subtilis and (closely) related micro-organisms have met with little success. Overexpression of particular members of the B. subtilis secretion machinery, especially of chaperone-like proteins which are the rate-limiting step in the secretion pathway would solve this problem. It is to be understood that the terms "chaperone" and "secretion factor" are not completely clearly defined. Both groups of proteins will at least overlap and in some cases may be identical. Because the mechanism of action of these proteins is not yet clearly understood, both terms will be used interchangeably herein.

SUMMARY OF THE INVENTION

The invention thus provides a proteinaceous substance comprising at least a functional part of a chaperone-like protein expressed by Gram-positive bacteria encoded by the ftsY gene of said bacteria, a representative of said gene being defined by the sequence of seq. ID no. 7.

When Gram-positive bacteria, especially Bacillus species and in particular Bacillus subtilis and its closely related organisms are provided with this proteinaceous substance, of which the functionality is defined as being able to recognize a protein of interest to be secreted and lead it into the secretory pathway, they will have an enhanced capability of secreting proteins. It is very likely that proteins to be secreted must have a signal sequence, which may be their own signal sequence, or a signal sequence of a homologous protein of the host bacteria or a signal sequence homologous to the micro-organism from which the proteinaceous substance, i.e. the secretion factor according to the invention is derived.

The protein of interest may be any protein which up until now has been considered for expression in prokaryotes, as long as it can be provided or has of its own a signal sequence which render it suitable for secretion in a Gram-positive host. Of course it must also be able to be recognized (if possibly not very efficiently) and lead into the secretory pathway by the chaperone-like proteins according to the invention. It may not be the case that the chaperone-like proteins would be capable of recognizing and leading into secretion each and every protein by itself. Other secretion factors may become the rate-limiting step, if the presently invented secretion factor is provided in sufficient quantities. In that case it is preferred to also provide the hosts with the secretion factors which may become the rate-limiting step in sufficient quantities also. Since we believe that there is a SRP-like route in Bacillus species and other gram-positive bacteria, it would be advantageous to provide the micro-organism with enhanced amounts of FtsY, the 7S scRNA and Ffh.

The protein of interest may be either homologous or heterologous to the host. In the first case overexpression should be read as expression above normal levels in said host. In the latter case basically any expression is of course overexpression.

The proteinaceous substance according to the invention, which for convenience will often be referred to as the chaperone, secretion factor or the chaperone-like protein, may be homologous to the host, which is preferred, but it may also be heterologous to the host, as long as it is compatible with the secretion machinery of the host. It stands to reason that this will be most likely in closely related organisms. Thus in the case of a Bacillus subtilis secretion factor, it would be preferred to use it in a Bacillus.

The sequence being depicted as giving a representative of a sequence encoding a chaperone-like protein according to the invention is given in order to enable the person skilled in the art to find homologous sequences which encode similar or functionally the same chaperone-like proteins in other Gram-positive bacteria, in particular of other Bacillus species. Given the general level of skill in the art, it will be routine work to prepare for instance primers based on the given sequence and to screen for other homologous sequences encoding said chaperone-like proteins. These chaperone-like proteins from other related organisms should therefore be considered as part of the present invention. Their DNA and/or amino acid sequences usually will be quite homologous. As a rule the homology will be greater then 70% overall, in particular homologies of greater than 85% overall are to be expected. It is understood that all homologous genes which can hybridize with the sequence depicted in seq. ID no. 7 and which encode a protein of essentially the same structure or function are comprised in this invention. The following equation, which has been derived from analyzing the influence of different factors on hybrid stability:

Tm=81+16.6 (log10 Ci)+0.4 (% G+C)−600/n−1.5% mismatch (Ausubel et al., supra) where n=length of the shortest chain of the probe Ci=ionic strength (M)

G+C=base composition, can be used to determine which level of homology can be detected using DNA—DNA hybridisation techniques.

Therefore the term "essentially of a structure" is intended to embrace sequences which can include conservative mutations, where the sequence encodes the same amino acid, but which may differ by up to 35% in the DNA sequence according to the above equation, more typically by up to 10%. It is not always necessary to have a complete chaperone-like protein to perform the functions of recognizing the protein to be secreted and leading said protein into the secretion pathway. Where possible the hosts may thus also be provided with functional parts of said secretion factor. It is also possible and even likely that association with non-protein material such as the 7S RNA may occur when the secretion factor performs its functions. The term proteinaceous substance is chosen to include such associations. It is by now well known in the art that mutations in proteins may lead to higher activity, longer half-lives, better stability of the mutated protein. Such derivatives of the secretion factors according to the invention are also part thereof, since given the information presented herein, it is routine work to find weak spots, or other sites interesting for mutation in the secretion factors according to the invention and making site-directed mutations.

A preferred embodiment of the present invention is a proteinaceous substance which is a chaperone-like protein which is at least partly encoded by the ftsY gene of a Bacillus species. Bacillus species are highly preferred organisms to express genes of interest in and a lot of developmental and production experience is available. As stated before however, there has always been a problem with secretion of especially heterologous proteins from Bacillus. This problem may in many cases be solved by providing Bacillus organisms with chaperone-like proteins from other related species, but it will be clear that chances of a good functional secretion factor in Bacillus, including recognition of the heterologous protein are highest using a chaperone-like protein which is derived from a secretion factor in a Bacillus species. Of special interest as a chaperonelike protein is a proteinaceous substance which is at least partly encoded by the ftsY gene of *Bacillus subtilis* or another Bacillus species. These proteinaceous substances are very likely to be analogues of the eukaryotic docking protein (or SRP receptor) as is the case with products derived from the *E. coli* ftsY gene. Lack of sufficient amounts of this chaperone-like protein will definitely have a great influence on the capability of host micro-organisms to secrete any proteins, let alone heterologous proteins. At present we believe that heterologous protein may be predominantly secreted using the SRP-like route, i.e. by binding to Ffh, the 7s RNA and the FtsY, whereas homologous proteins use the general secretion pathway. It is also clear that if a heterologous protein to be secreted is provided with a signal homologous or very closely related to a signal present in Bacillus secretory proteins that the presence of a sufficient amount of the secretion factor which normally has the function of recognizing such a signal will lead to enhanced secretion.

The preferred method of providing a Gram-positive bacteria, in particular a Bacillus species with the possibility of expressing sufficient amounts of the chaperone-like proteins (and for instance scRNA) according to the invention is of course by providing said micro-organism with the genetic information to overexpress said chaperone-like protein. The invention therefor also provides a recombinant DNA molecule comprising at least a part of an ftsY gene encoding a chaperone-like protein of Gram-positive bacteria, said part encoding at least a functional part of said chaperone-like protein, whereby a representative of said gene has the sequence of seq. ID no. 7.

As is true for the proteinaceous substances of the invention the given sequence is given for the reason of enabling the skilled person to find homologous sequences encoding similar secretion factors. Variants may exist within Bacillus species and other Gram-positive bacteria. It will also enable the person skilled in the art to construe silent mutations, to construe beneficial mutations or mutations having no effect on the activity of the chaperone resulting from expression. For different species codon preference may de different, degeneracy may be accounted for. All these modifications should be considered to be within the scope of the present invention. To define which genes still belong to the invention can really only be done by their functionality. If they encode a substance which has the same activity (in kind, not in amount) as the presently invented chaperone-like proteins then the gene (or the recombinant DNA molecule) should be considered to belong to the present invention, if the molecule is derived from a Gram-positive bacteria, in particular a Bacillus species. Usually this will coincide with a rather high degree of homology for instance of 70–95% overall.

A further preferred embodiment of the present invention is of course a gene or a recombinant DNA molecule comprising at least a part of the ftsY gene of a Bacillus species. The main reason for this preference is of course that Bacillus species are well known production organisms in which for reasons already mentioned it would be helpful to provide an autologous (sometimes also called homologous) chaperone-like protein. The most preferred chaperone-like protein at the present time is the one encoded by a recombinant DNA molecule comprising at least a part of the ftsY gene of *Bacillus subtilis*.

For easy transfer of the genetic information of the secretion factors according to the invention it is preferred to provide the recombinant DNA molecule as a vector. The invention thus also provides a recombinant vector comprising a recombinant DNA molecule as disclosed above and suitable regulatory elements for replication and/or expression. The nature and kind of such a vector is not important, as long as it is capable of transferring the wanted genetic information into the desired micro-organism and preferably being capable of replicating or being replicated in such micro-organism. They may comprise many additional advantageous features such as marker genes, restriction sites, etc. Chromosonal integration of (part of) the gene according to the secretion factor is also comprised within this invention. It would of course be advantageous to only have to transfer a micro-organism with one vector. Preferably the invention provides a recombinant vector as described above further comprising a gene encoding a protein of interest to be secreted.

The invention further provides micro-organisms which have been provided with the genetic information to encode a chaperone-like according to the invention by whatever method. The invention thus includes a cell derived from a Gram-positive host cell comprising a recombinant DNA molecule or a vector as defined herein before. Preferably the cell is derived from a Bacillus species.

In a further preferred embodiment the cell has also been provided with the ability to overexpress either or both 7S scRNA and Ffh in a similar manner as it has been provided with the (over)expression of FtsY.

In a further preferred embodiment the cell also has been provided with the ability to overexpress a homologous protein or to express a heterologous protein. A suitable way to arrive at such a cell is providing it with the genetic information for said protein of interest, leading to a cell comprising a vector having the genetic information encoding a chaperone-like protein according to the invention, further comprising a vector comprising a gene encoding a protein of interest to be secreted. All methods leading to the products of the invention are of course also part of this invention. In particular important are the methods leading to the enhanced production of proteins secreted in the culture medium. The invention thus also includes a method for enhancing the secretion of a protein of interest from a Gram-positive micro-organism, comprising the steps of providing said micro-organism with the possibility to over express the protein of interest, providing the micro-organism with the possibility of overexpressing a proteinaceous substance according to the invention, and culturing said micro-organism under suitable conditions.

Preferably the possibility to overexpress the protein of interest is provided by a vector as disclosed herein before and the possibility to overexpress a proteinaceous substance according to the invention is also provided by a vector as disclosed hereinabove.

The invention will now be further illustrated in the following detailed description and the examples.

BRIEF DESCRIPTION OF THE DRAWINGS

FIGS. 1A–1B. FIG. 1A shows the plasmids pHB201 and pHBNde described in Example 1. FIG. 1B shows the plasmid pHBChap.

FIGS. 2A (SEQ ID NOs: 9–13) and 2B (SEQ ID NOs: 14–19) illustrate sequence homology among various ORFs as described in Example 2.

FIGS. 3A–D shows the molecular features and the DNA sequence (SEQ ID NO:20) of the Pst I fragment described in Example 3 .

FIG. 4 illustrates the GTP binding boxes of SRα like proteins as described in Example 3.

FIG. 5 shows the chromosomal organization of the genes in the Pst I fragment described in Example 3.

FIG. 6 shows the integration construct pNS' as described in Example 4.

FIG. 7 illustrates the double cross-over event as described in Example 5.

FIG. 8 illustrates the chromosomal organization of an isolated integrant strain as described in Example 5.

FIG. 9 shows an SDS PAGE of h-IL-3 as described in Example 7.

DETAILED DESCRIPTION OF THE INVENTION

There is now growing evidence that poor expression and/or secretion is caused by incorrect folding of the heterologous protein in the host cell. The cause of this effect may be the incompatibility of the host cell's chaperone-like proteins of the regular secretory pathway and the heterologous protein. As a result the newly synthesized heterologous proteins will be recognized very inefficiently and in this way become a rate-limiting step in the translocation process. This will be even more pronounced if the heterologous protein is overexpressed. One possibility to overcome this problem is to express heterologous chaperone-like proteins which are homologous to the heterologous protein which is to be secreted. Expression of E. coli SecB in B. subtilis has shown to facilitate secretion of the SecB-dependent maltose-binding protein of E. coli (Collier, 1994). This option is probable not applicable when the heterologous protein and secretion factor are from a more phylogenetic distant organism. In this way the host cell's regular secretion machinery could become incompatible with the heterologous chaperone-like protein itself, leaving the same effect: extreme low secretion efficiency. Another possibility, part of this invention, is to overexpress one or more of the host cell's chaperone-like proteins, preferably the SRP-like chaperone-like proteins and so increase the availability of these chaperone-like proteins for the heterologous protein.

Because homologues of SecA (Sadaie et al. 1991), SecE (Jeong et al. 1993), SecY (Su et al. 1990), and Lep (Van Dijl et al. 1992) have been identified in B. subtilis, it is suggested that signal peptide-dependent protein secretion in B. subtilis utilizes a Sec-pathway that is similar to that of E. coli. So far SecB, which is considered to be the major chaperone in E. coli, seems to be the only chaperone which has a direct binding affinity for SecA and so contributes to the accurate targeting of the preprotein-SecB complex to the membrane bound translocase. The SecB protein is needed for only a subset of the envelope proteins so SecB independent proteins will enter the Sec-pathway with the aid of helper proteins like GroEL/GroES, DnaK/DnaJ or other proteins like SRP. In eukaryotic organism SRP mainly is responsible for the translocation across the ER membrane. Recently more evidence has become available of the existence of an SRP mediated secretion route in bacteria. Because the eukaryotic pathway has probably evolved from the bacteria it is thinkable that said proteins are also dependent on this pathway when said proteins are expressed in bacteria like Bacillus. Thus optimisation of this particularly pathway in Bacillus will be more profitable for heterologous (eukaryotic) proteins secretion than the optimisation of the well known sec-pathway. This invention relates to the cloning of the Bacillus ftsY gene and its effect after (over)-expression, alone or in combination with other members of the bacterial SRP, upon heterologous proteins.

For the cloning of B. subtilis ftsY degenerate primers were synthesized making use of the existing homology boxes between the Srα homologues of different organism (FIG. 2a, SEQ ID NOs: 9–13). After an inversed PCR reaction using a 110 bp fragment, which was derived from a nested PCR reaction, as template a 4 kb fragment could be detected. Sequencing results (FIG. 2b, SEQ ID NOs: 14–19) revealed an open reading frame of 329 amino acids. This protein shared 48.2% amino acid identity and 65% similarity with the ftsY gene of E. coli.

As will be shown in the Examples, the hybridizing experiments originally lead to an unwanted result, i.e. a smear of indistinct bands. Surprisingly, we were able by cutting out a region around the expected size of the amplified fragment and applying PCR to that region again in resolving this smear into a group of distinct bands. Unfortunately hardly any band was seen at the expected size of the fragment that should have been amplified. However, in a third round of amplification we were nevertheless able to obtain a fragment which could be used further.

EXAMPLE 1

Construction of a Promoter Vector for Secretion Factor Overexpression pHB201 is capable of autonomous replication in both E. coli (high-copy) and Bacillus (low-copy) strains. This plasmid confers resistance to the antibiotics chloramphenicol and erythromycin in E. coli and Bacillus. Further the plasmid carries a CAT86::lacZ fusion gene preceded by the strong Lactococcus lactis promoter 59 which also act as strong promoter in B. subtilis (Van der Vossen et al. 1987).

By replacing the SalI/EcoRI fragment of this plasmid by a synthetic DNA fragment (SEQ ID NO:1) the CAT86::lacZ was deleted and an unique NdeI restriction site introduced overlapping the translation initiation site generating pHBNde (FIG. 1a). This allows us to express the chaperone genes directly downstream the strong Lactococcal promoter 59 without creating fusion proteins as would be with the orginal pHB201 vector (FIG. 1b).

EXAMPLE 2

Molecular Cloning of Bacillus subtilis DNA Fragments Homologous With the Human SRα Gene A set of three Polymerase Chain Reactions (PCR) were performed as follows. Chromosomal DNA of B. subtilis 168 was used as template in a first PCR reaction with degenerate primers AB4229 (SEQ ID NO: 2) and AB4230 (SEQ ID NO: 3). After 30 cycles and an annealing temperature of 40° C. the amplified DNA was fractionised by electrophoresis on a 2% Metaphor (FMC BioProducts) agarose gel. The results showed a smear of ill resoluted bands. DNA fragments ranging in size from 220 bp to 300 bp were purified from the agarose gel with a QIAquick gel extraction column (QIAGEN).

1/50 of these isolated fragments were used in a second PCR with degenerate primers AB4229 and AB 4241 (SEQ ID NO: 4) using the same reaction conditions as in the first PCR. The result of this PCR showed a number of district bands, however, a band of the expected size (±120 bp) was hardly visible. Fragments of ±120 bp were isolated from the agarose gel as above and used in a third PCR with the same primers and conditions as were used for the second PCR. The resulting single fragment was isolated, purified and after treatment with T4 polynucleotide kinase ligated into dephosphorylated pUC18 linearized with SmaI.

After electroporation to $E.$ $coli$ JM109, selection IPTG/X-gal plates, the DNA from six white colonies were used for automated sequencing. Within all six isolates an Open Reading Frame (ORF) could be detected. This ORF showed over 70% similarity with an alignment of homologs from several other organisms (FIG. 2b, SEQ ID NOs: 14–19).

EXAMPLE 3

Sequencing of Unknown DNA Sequences Adjacent to a Short Stretch of Known Sequence By using a labelled internal ftsY fragment derived from example 2 we could detect a single 4 kb PstI band in a hybridisation experiment. None of the attempts to clone this fragment directly into pUC were successful, indicating that cloning of this fragment could be lethal in $E.$ $coli$. An inversed PCR (IPCR) was used for determination of the sequence.

A total PstI digest of $B.$ $subtilis$ 168 chromosomal DNA was used as template in the IPCR with primers AB5356 (SEQ ID NO: 5) and AB5357 (SEQ ID NO: 6). The resulting fragment was used directly for automated sequencing making use of the same primers. The sequence of the rest of the PstI chromosomal DNA fragment located upstream of the primer AB5357 and downstream of primer AB5357 was determined by automated sequencing making use of newly developed primers while the sequence was unveiled. The total 4370 bp DNA sequence of the PstI fragment is shown in FIG. 3 (SEQ ID NO: 3).

Analysis of the sequence showed the presence of several Open Reading Frames (ORFs), including the one for FtsY. When comparing the overall structure of the SRα like proteins and SRP54-like proteins a common domain is evident which comprises GTP binding boxes (the G-domain, see FIG. 4). Also from this figure it is clear that the $B.$ $subtilis$ FtsY protein contains only a very short N-terminal domain, in contrast to the eukaryotic and $E.$ $coli$ homologues. Since the N-terminal domain in those organisms serves as a membrane anchor it is possible that in $B.$ $subtilis$ FtsY functions with a different mechanism, and is possibly more chaperone-like in its action, although it may still be membrane-bound.

Analysis of the sequence showed the presence of several more ORF's, including a truncated ORF showing homology to the Ffh protein, and a truncated ORF showing homology to several DNA segregation proteins like the Yeast protein SMC1.

The chromosomal organisation of the genes in the PstI fragment is shown in FIG. 5.

EXAMPLE 4

Effect of FtsY Depletion Upon the Secretion of Heterologous Proteins

The effects of depletion of FtsY in Bacillus on the processing and/or secretion of heterologous proteins were studied by placing the chromosomal ftsY gene under control of the inducible SPAC promoter (Yansura et. al). For this the N-terminal part of the ftsY gene was cloned into the multiple cloning site of pDG148 directly downstream the SPAC promoter. The SPAC-ftsY-penP-lacI fragment from the resulting pDGFtsY' plasmid was recloned into pPPNeo2 making the final integration construct pNSFtsY' (FIG. 6).

pNSFtsY' is capable of autonomous replication in $E.$ $coli$ but not in Bacillus. It confers resistance to the antibiotic ampicillin which can be used for selection in $E$ $coli$ and neomycin for selection in Bacillus. Integration of pNSFtsY' into the ftsY locus results in a truncated copy of ftsY (ftsY') under control of the authentic promoter and an intact copy of ftsY under control of the SPAC promoter.

Neomycin resistant pNSFtsY' integrants could be selected after a protoplast transformation of $B.$ $subtilis$ 168. Integrants growing in a medium with 0.5 mM IPTG showed growth characteristics comparable to $B.$ $subtilis$ host lacking the integrated plasmid. The growth rate of integrants did not decrease after incubation in the absence of IPTG, nor did the cell morphology.

Effects of depletion of FtsY on protein translocation were examined by fermentation experiments using hosts expressing heterologous proteins. A pUB110 like vector containing regulatory sequences of the $B.$ $licheniformis$ or $B.$ $amyloliquefaciens$ α-amylase gene was used for the expression of heterologous proteins. Some of the heterologous proteins were produced to slightly higher levels in cells cultured in the presence of IPTG, however in the absence of IPTG the production of the heterologous proteins was not completely abolished.

These effects were unexpected since in $E.$ $coli$ depletion of FtsY has a profound effect on the cell morphology and growth rate. Therefore it is possible that there is FtsY formation despite the absence of IPTG, indicating transcriptional read through. It should be possible to correct this by insertion of a strong terminator signal upstream of the SPAC promoter in the integration construct. To confirm that the absence of FtsY is hazardous to the cell attempts were made to disrupt the ftsY gene.

EXAMPLE 5

Construction of Bacillus Strains without a Functional ftsY Gene

Since the experiments described in Example 4 were unexpected in the sense that strain containing the ftsY gene under the control of the SPAC promoter were still viable, and showed no clear phenotype in the absence of the inducer IPTG, we hypothesized that the construct we used was leaky so that even in the absence of IPTG a small amount of FtsY would be produced. To eliminate the production of FtsY we tried to disrupt the ftsY gene by insertion of a neomycin resistance marker. We constructed a plasmid pBHdSFtsY-Neo which harbours the 5' and the 3' end of the ftsY gene separated by the Neomycin resistance gene in a vector unable to replicate in $B.$ $subtilis$.

Plasmid pBHdSFtsYNeo was linearized by cutting with HpaI and used to transform B. subtilis 168 to neomycin resistance. This should lead to strains having the original ftsY gene replaced by the fstY::Neo construct via a double cross-over event (see FIG. 7). However, we were unable to select for Neomycin resistant colonies using this linear DNA, suggesting the possibility that disruption of the ftsY gene is lethal to the cell.

We therefore repeated the transformation experiments with intact, uncut, plasmid DNA. In this case integration of the plasmid into the ftsY gene can take place via a single cross-over event (Campbell type integration), leading to neomycin resistant colonies which have both an intact and a disrupted copy of the ftsY gene present (see FIG. 8). We isolated integrant strains, one of which was shown to have the chromosomal organization represented in FIG. 8. Since in this strain two copies of the 3' end of the fstY gene are present recombination between them is possible, leading to excision of the plasmid sequences in between and formation of a strain containing only one copy of the ftsY gene, disrupted by the neomycin resistance marker. Despite several attempts we were unable to isolate such recombinant strains, suggesting again that such strains are unviable.

EXAMPLE 6

Effect of FtsY Overexpression on the Location of Precursors and Mature Heterologous Proteins The effects of overexpression of FtsY in Bacillus on the processing and/or secretion of heterologous proteins were studied by placing the complete ftsY gene under control of the constitutive P59 promoter in pHBNde (see Example 1) resulting in the plasmid pHBFtsY. Effects of overexpression of FtsY on protein translocation were examined by pulse-chase experiments using hosts expressing heterologous proteins.

B. Licheniformis T399 was transformed with plasmid pLAT-IL3 containing the human Interleukin-3 (h-IL-3) gene expressed from the B. licheniformis α-amylase promoter and provided with the B. licheniformis α-amylase signal sequence, or with the plasmid pLP10-AB containing the prochymosin gene under the same expression signals. The resulting strains T399IL and T399Chy were transformed with plasmid pHBNFtsY containing the ftsY gene. As a control also both strains T399IL and T399Chy were transformed with the vector pHBNde.

Single colonies of all strains were inoculated in 5 ml of medium starvation medium S7+ (including Methionine and Cysteine) and grown at 37° C. overnight. Aliquots of 200 µg were inoculated in 5 ml S7– (without Methionine and Cysteine) medium and grown for another 5 hours.

After growth to OD=0.3–0.7 a sample of 3.2 ml was centrifuged, washed with S7– medium and resuspended into 3.2 ml fresh S7– medium. The sample was incubated for 20 minutes at 37° C. and pulsed with 25µ(Ci L-[$^{35}$S]-Methionine (>1000 Ci/mmol) per ml during 60 seconds at 37° C. Then a chase was performed by addition of 50 µl (2 mg/ml) L-Methionine per ml. The chase was stopped at different time points (0, 15, 30, and 60 seconds) by mixing of 600 µl of the reaction with 600 µl ice cold 20% TCA, and incubation on ice for at least 30 minutes. The samples were centrifugated, and the supernatant was used directly for immuno precipitation, SDS-polyacrylamide gel electrophoresis and autoradiography using standard protocols.

The cell pellet was washed with 1 ml aceton, and dried. The cells were resuspended in 50/1 lysis buffer 10 mM Tris pH 8, 25 mM MgCl, 200 mM NaCl, 5 mg/ml lysozyme) and incubated for 3 minutes at 37° C. After addition of 50 µl TES (20 mM Tris, 2 mM EDTA, 2% SDS, pH 8) the samples were boiled for 5 minutes. To the samples was added 900µl of STDT (10 mM Tris, 0.9% NaCl, 1% Triton, 0.5% Sodium deoxycholate, pH8.2), the mixture was incubated for 15–60 minutes on ice, and the debris was precipitated. The supernatant was used for immuno precipitation with antiserum raised against h-IL-3 or Chymosin and subsequent SDS-polyacrylamide gel electrophoresis and autoradiography using standard protocols.

Overexpression of FtsY increased the secretion of the mature form of interleukin-3 and the processing of the precursor of prochymosin.

EXAMPLE 7

Effect of Overexpression of Ffh on the Secretion of Human Interleukin-3

The ffh gene encoding the B. subtilis homologue of the eukaryotic SRP54 protein was cloned as a PCR fragment obtained using primers based on the published DNA sequence (Honda et al, 1993). The gene was cloned into the vector pHBNde (see Example 1) under the control of the strong Lactococcal P59 promoter to form plasmid pHBN-Ffh.

Pulse-chase experiments were performed as described in Example 6 with B. licheniformis strains containing both plasmid pHBNffh and plasmid pLAT-IL3 harbouring the human Interleukin-3 (h-IL-3) gene under the expression and secretion signals of the B. licheniformis α-amylase gene.

As is shown in FIG. 9, the processing of h-IL-3 is very fast, as no precursor can be detected. The amount of mature h-IL-3 in the supernatant fraction is in all cases higher in the samples obtained from the strain overproducing Ffh compared to the strain containing only the vector plasmid.

EXAMPLE 8

Effects of Overexpression of scRNA on the Secretion of Human Interleukin-3

The scr gene encoding the scRNA from B. subtilis was cloned as a PCR fragment using primers based on the published DNA sequence (Struck et al, 1989) and following the approach (including the same 5' primer) described by Nakamura (Nakamura et al, 1992) introducing a HindIII site just upstream of the scr DNA and a SphI site downstream of the terminator sequence.

The P59 promoter was deleted from the vector pHB210 by replacement of the AlwNI-SmaI fragment containing the origin of replication (ori) together with the P59 promoter by the AlwNI-PvuII fragment from vector pBR322 containing only the same ori. This new vector pBHk was used to exchange the EcoRI-PvuII fragment for the EcoRI-BamHI (blunted by T4 polymerase) containing the SPAC-penP-lacI cassette from pDG148 to contruct the vector pBHSpac.

The PCR fragment containing the scr gene was digested with HindIII and SphI and ligated into pBHSpac digested with the same restriction enzymes to contruct plasmid pBHSscr. This way the scr gene was placed under the control of the SPAC promoter.

Pulse-chase experiments were performed as described in Example 6 with B. licheniformis strains containing both plasmid pBHSscr and plasmid pLAT-IL3 harbouring the human Interleukin-3 (h-IL-3) gene under the expression and secretion signals of the B. licheniformis α-amylase gene.

Also in this case the processing of h-IL-3 was very fast, as no precursor could be detected. However, the amount of mature h-IL-3 in the supernatant fraction was in all cases higher in the samples obtained from the strain overproducing scRNA compared to the strain containing only the vector plasmid, or with plasmid pBHSscr in the absence of the inducer IPTG.

EXAMPLE 9

Effects of Simultaneously Overexpressed Signal Recognition Particle components on the Secretion of Heterologous Proteins The effects described in Examples 6, 7 and 8 were even more pronounced when more than one of the components of the bacterial signal recognition particle were simultaneously expressed. For this purposs the ftsY gene was expressed from the IPTG inducible promoter located in the chromosome as described in Example 4 by addition of 3 mM IPTG, while the components Ffh or scRNA were expressed from their pHB210 derived vectors described in Examples 7 and 8 above.

REFERENCES

Ausubel et al. (1987), Current Protocols in Molecular Biology, John Wiley and Sons Inc., New York.
Bernstein, H. D., M. A. Poritz, K. Strub, P. J. Hoben, S. Brenner, and P. Walter. 1989. Nature (London) 340, 482–486.
Collier, D. N., 1994. J. Bacteriol. 176, 1937–1940.
Gilmore, R., 1993. Cell 75, 589–592.
Hann, B. C., M. A. Poritz, and P. Walter. 1989. J. Cell Biol. 109, 3223–3230.
Hartl, F-U., S. Lecker, E. Schiebel, J. P. Hendrick, and W. Wickner. 1990. Cell 63, 269–279.
Honda, K., K. Nakamura, M. Nishiguchi, and K. Yamane. 1993. J. Bacteriol. 175, 4885–4894.
Jeong, S. M., H. Yoshikawa, and H. Takahashi. 1993. Mol. Microbiol. 10, 133–142.
Kim, Y. J., T. Rajapandi, and D. Oliver. 1994. Cell 87, 845–853.
Kumamoto, C. A., and J. Beckwith. 1983. J. Bacteriol. 154, 253–260.
Kumamoto, C. A., and J. Beckwith. 1985. J. Bacteriol. 163, 267–274.
Lill, R., W. Dowhan, and W. Wickner. 1990. Cell 60, 259–269.
Luirink, J., S. High, H. Wood, A. Giner, D. Tollerrey, and B. Dobberstein. 1992. Nature 359, 741–743.
Luirink, J., C. M. ten Hagen-Jongman, C. C. van der Weyden, B. Oudega, S. High, B. Dobberstein, and R. Kusters. 1994. EMBO J. 13, 2289–2296.
Nakamura K., Y. Imai, A. Nakamura, and K. Yamane. 1992. J. Bacteriol. 174, 2185–2192.
Oliver, D. B., and J. Beckwith. 1981. Cell 25, 765–772.
Poritz, M. A., K. Strub, and P. Walter. 1988. EMBO J. 3, 3303–3310.
Ribes, U., K. R^misch, A. Giner, B. Dobberstein, and D. Tollerrey. 1990. Cell 63, 591–600.
Romisch, K., J. Webb, J. Herz, S. Prehn, R. Frank, M. Vingron, and B. Dobberstein. 1989. Nature 340, 478–482.
Sadaie, Y., H. Takamatsu, K. Nakamura, and K. Yamane. 1991. Gene 98, 101–105.
Samuelsson, T. 1992. Nucleic Acids Res. 20, 5763–5770.
Schiebel, E., A. J. M. Driessen, F-U. Hartl, and W. Wickner. 1991. Cell 64, 927–939.
Struck, J. C. R., R. K. Hartmann, H. Y. Toschka, and V. A. Erdmann. 1989. Mol. Gen. Genet. 215, 478–482.
Struck, J. C. R., and V. A. Erdmann. 1990. Eur. J. Biochem. 192, 17–24.
Su, J-W., A. Boylan, S. M. Thomas, K. M. Dolan, D. B. Oliver, and C. W. Price. 1990. Mol. Microbiol. 4, 305–314.
Van der Vossen, J. M. B. M., D. van der Lelie, and G. Venema. 1987, Appl. Environ. Microb. 53, 2452–2457.
Van Dijl, J. M., A. de Jong, J. Vehmaanpera, G. Venema, and S. Bron. 1992. EMBO J. 11, 2819–2828.
Yansura, D. G., and D. J. Henner. 1984. Proc. Natl. Acad. Sci. 81, 439–443.

What is claimed is:

1. A host cell comprising an expression vector comprising a polynucleotide encoding the amino acid sequence of SEQ ID NO:8.

2. A host cell comprising an expression vector comprising a polynucleotide having the amino acid sequence of SEQ ID NO:7.

3. The host cell of claim 1, wherein said host cell is a member of the genus Bacillus.

4. The host cell of claim 2, wherein said host cell is a member of the genus Bacillus.

5. The host cell of claim 1, wherein said host cell is a member of the genus Bacillus selected from the group consisting of *Bacillus subtilis, Bacillus amyloliquefaciens, Bacillus alcalophilus, Bacillus centus* and *Bacillus stearothermophilus.*

6. The host cell of claim 2, wherein said host cell is a member of the genus Bacillus selected from the group consisting of *Bacillus subtilis, Bacillus amyloliquefaciens, Bacillus alcalophilus, Bacillus centus* and *Bacillus stearothermophilus.*

7. The host cell of claim 1, further comprising a polynucleotide encoding a protein of interest.

8. The host cell of claim 2, further comprising a polynucleotide encoding a protein of interest.

9. The host cell of claim 7, further comprising a polynucleotide encoding a Bacillus Ffh protein.

10. The host cell of claim 8, further comprising a polynucleotide encoding a Bacillus Ffh protein.

11. The host cell of claim 7, further comprising a polynucleotide encoding a Bacillus scRNA.

12. The host cell of claim 8, further comprising a polynucleotide encoding a Bacillus scRNA.

* * * * *

SEQUENCE LISTING

```
<160> NUMBER OF SEQ ID NOS: 20

<210> SEQ ID NO 1
<211> LENGTH: 170
<212> TYPE: DNA
<213> ORGANISM: Artificial Sequence
<220> FEATURE:
<223> OTHER INFORMATION: synthetic

<400> SEQUENCE: 1
gctctagagt agatctgcag gctttaacgt aggcaaagct cagggtagac tttgaatgga      60
cagaaacatg acatatctct tgaaaggatg attgtggtgg tgaaaacaga taaaatctcc     120
tcctgaatac agtaaatcac attcaggagg agatacatat ggaattcgta                170

<210> SEQ ID NO 2
<211> LENGTH: 20
<212> TYPE: DNA
<213> ORGANISM: Artificial Sequence
<220> FEATURE:
<223> OTHER INFORMATION: degenerate primer based on Bacillus subtilis
      sequence
```

```
<400> SEQUENCE: 2
ggmgtsaayg gmgtsggmaa                                            20

<210> SEQ ID NO 3
<211> LENGTH: 20
<212> TYPE: DNA
<213> ORGANISM: Artificial Sequence
<220> FEATURE:
<223> OTHER INFORMATION: degenerate primer based on Bacillus subtilis
      sequence

<400> SEQUENCE: 3
gcrscygsrc grwakrtrtc                                            20

<210> SEQ ID NO 4
<211> LENGTH: 17
<212> TYPE: DNA
<213> ORGANISM: Artificial Sequence
<220> FEATURE:
<223> OTHER INFORMATION: degenerate primer based on Bacillus subtilis
      sequence
<220> FEATURE:
<221> NAME/KEY: misc_feature
<222> LOCATION: (1)...(17)
<223> OTHER INFORMATION: n = A,T,C or G

<400> SEQUENCE: 4
arnckkccng cygtrtc                                               17

<210> SEQ ID NO 5
<211> LENGTH: 34
<212> TYPE: DNA
<213> ORGANISM: Artificial Sequence
<220> FEATURE:
<223> OTHER INFORMATION: primer based on Bacillus subtilis sequence

<400> SEQUENCE: 5
tgcctgtcat taagcagacg gcaggaagcg atcc                            34

<210> SEQ ID NO 6
<211> LENGTH: 34
<212> TYPE: DNA
<213> ORGANISM: Artificial Sequence
<220> FEATURE:
<223> OTHER INFORMATION: primer based on Bacillus subtilis sequence

<400> SEQUENCE: 6
tttgctcatc tccgctgtta taaatctcga ccag                            34

<210> SEQ ID NO 7
<211> LENGTH: 1015
<212> TYPE: DNA
<213> ORGANISM: Bacillus subtilis
<220> FEATURE:
<221> NAME/KEY: CDS
<222> LOCATION: (19)...(1008)
<223> OTHER INFORMATION: protein secretion chaperone

<400> SEQUENCE: 7
gaggaaagag gttaaaag atg agc ttt ttt aaa aaa tta aaa gag aaa atc   51
                    Met Ser Phe Phe Lys Lys Leu Lys Glu Lys Ile
                     1               5                  10 aca aaa cag aca gat tcc gta tct gaa aag ttt aag gat ggc ctt gaa   99
Thr Lys Gln Thr Asp Ser Val Ser Glu Lys Phe Lys Asp Gly Leu Glu
             15                  20                  25
```

```
                                                        -continued aaa aca aga aac tcc ttt caa aac aaa gtg aat gat ctt gta tcc cgt      147
Lys Thr Arg Asn Ser Phe Gln Asn Lys Val Asn Asp Leu Val Ser Arg
        30                  35                  40 tac cgt aaa gtg gat gag gat ttc ttc gaa gag ctt gaa gag gtt ctt      195
Tyr Arg Lys Val Asp Glu Asp Phe Phe Glu Glu Leu Glu Glu Val Leu
 45                  50                  55 atc agc gcg gat gtc ggt ttt aca acc gtt atg gaa tta ata gat gag      243
Ile Ser Ala Asp Val Gly Phe Thr Thr Val Met Glu Leu Ile Asp Glu
 60                  65                  70                  75 ctg aaa aaa gaa gtc aaa cgc aga aat att caa gat cca aag gaa gtc      291
Leu Lys Lys Glu Val Lys Arg Arg Asn Ile Gln Asp Pro Lys Glu Val
                 80                  85                  90 aag tca gtg att tct gag aaa ctg gtc gag att tat aac agc gga gat      339
Lys Ser Val Ile Ser Glu Lys Leu Val Glu Ile Tyr Asn Ser Gly Asp
             95                 100                 105 gag caa att tca gaa ctg aac atc cag gat ggg cgt tta aac gta atc      387
Glu Gln Ile Ser Glu Leu Asn Ile Gln Asp Gly Arg Leu Asn Val Ile
        110                 115                 120 ctt ctg gta ggt gta aac ggc gtc ggg aaa aca aca acg atc gga aag      435
Leu Leu Val Gly Val Asn Gly Val Gly Lys Thr Thr Thr Ile Gly Lys
    125                 130                 135 ctt gct cat aaa atg aaa caa gaa gga aaa tct gtt gta ctt gcc gcc      483
Leu Ala His Lys Met Lys Gln Glu Gly Lys Ser Val Val Leu Ala Ala
140                 145                 150                 155 gga gac act ttt aga gcg gga gcc att gaa cag ctg gaa gta tgg gga      531
Gly Asp Thr Phe Arg Ala Gly Ala Ile Glu Gln Leu Glu Val Trp Gly
                160                 165                 170 gag cgt aca gga gtg cct gtc att aag cag acg gca gga agc gat ccg      579
Glu Arg Thr Gly Val Pro Val Ile Lys Gln Thr Ala Gly Ser Asp Pro
            175                 180                 185 gcg gct gtc atc tac gat gct gtt cat gct gcg aaa gca aga aat gcc      627
Ala Ala Val Ile Tyr Asp Ala Val His Ala Ala Lys Ala Arg Asn Ala
        190                 195                 200 gat gta tta att tgt gat acg gca ggg cgt ctc caa aac aaa gta aat      675
Asp Val Leu Ile Cys Asp Thr Ala Gly Arg Leu Gln Asn Lys Val Asn
    205                 210                 215 ctc atg aaa gag ctt gaa aaa gta aaa cgt gtt atc gaa aga gaa gtt      723
Leu Met Lys Glu Leu Glu Lys Val Lys Arg Val Ile Glu Arg Glu Val
220                 225                 230                 235 cct gaa gct ccg cat gag gtg ctg ctt gcc ctt gat gcc acg acc ggc      771
Pro Glu Ala Pro His Glu Val Leu Leu Ala Leu Asp Ala Thr Thr Gly
                240                 245                 250 caa aat gca atg gct cag gca aaa gaa ttc tct aaa gca aca aat gtt      819
Gln Asn Ala Met Ala Gln Ala Lys Glu Phe Ser Lys Ala Thr Asn Val
            255                 260                 265 acc ggc att gct tta acg aag ctt gac ggt acg gca aaa ggc ggt atc      867
Thr Gly Ile Ala Leu Thr Lys Leu Asp Gly Thr Ala Lys Gly Gly Ile
        270                 275                 280 gtc ctt gcg att cgc aac gag ctt cac atc ccg gtt aaa cta gtc ggt      915
Val Leu Ala Ile Arg Asn Glu Leu His Ile Pro Val Lys Leu Val Gly
    285                 290                 295 tta gga gaa aaa gtt gat gac ctt cag gaa ttt gat cca gaa tcc tat      963
Leu Gly Glu Lys Val Asp Asp Leu Gln Glu Phe Asp Pro Glu Ser Tyr
300                 305                 310                 315 gtg tac gga ctc ttt tca gat tta gtg gaa aaa gcc gac gat taa         1008
Val Tyr Gly Leu Phe Ser Asp Leu Val Glu Lys Ala Asp Asp *
                320                 325 gaaaaag                                                             1015
```

```
<210> SEQ ID NO 8
<211> LENGTH: 329
<212> TYPE: PRT
<213> ORGANISM: Bacillus subtilis

<400> SEQUENCE: 8
```

Met Ser Phe Phe Lys Lys Leu Lys Glu Lys Ile Thr Lys Gln Thr Asp
1               5                   10                  15

Ser Val Ser Glu Lys Phe Lys Asp Gly Leu Glu Lys Thr Arg Asn Ser
            20                  25                  30

Phe Gln Asn Lys Val Asn Asp Leu Val Ser Arg Tyr Arg Lys Val Asp
        35                  40                  45

Glu Asp Phe Phe Glu Glu Leu Glu Val Leu Ile Ser Ala Asp Val
    50                  55                  60

Gly Phe Thr Thr Val Met Glu Leu Ile Asp Glu Leu Lys Lys Glu Val
65                  70                  75                  80

Lys Arg Arg Asn Ile Gln Asp Pro Lys Glu Val Lys Ser Val Ile Ser
                85                  90                  95

Glu Lys Leu Val Glu Ile Tyr Asn Ser Gly Asp Glu Gln Ile Ser Glu
            100                 105                 110

Leu Asn Ile Gln Asp Gly Arg Leu Asn Val Ile Leu Leu Val Gly Val
        115                 120                 125

Asn Gly Val Gly Lys Thr Thr Thr Ile Gly Lys Leu Ala His Lys Met
130                 135                 140

Lys Gln Glu Gly Lys Ser Val Val Leu Ala Ala Gly Asp Thr Phe Arg
145                 150                 155                 160

Ala Gly Ala Ile Glu Gln Leu Glu Val Trp Gly Glu Arg Thr Gly Val
                165                 170                 175

Pro Val Ile Lys Gln Thr Ala Gly Ser Asp Pro Ala Ala Val Ile Tyr
            180                 185                 190

Asp Ala Val His Ala Ala Lys Ala Arg Asn Ala Asp Val Leu Ile Cys
        195                 200                 205

Asp Thr Ala Gly Arg Leu Gln Asn Lys Val Asn Leu Met Lys Glu Leu
    210                 215                 220

Glu Lys Val Lys Arg Val Ile Glu Arg Glu Val Pro Glu Ala Pro His
225                 230                 235                 240

Glu Val Leu Leu Ala Leu Asp Ala Thr Thr Gly Gln Asn Ala Met Ala
                245                 250                 255

Gln Ala Lys Glu Phe Ser Lys Ala Thr Asn Val Thr Gly Ile Ala Leu
            260                 265                 270

Thr Lys Leu Asp Gly Thr Ala Lys Gly Gly Ile Val Leu Ala Ile Arg
        275                 280                 285

Asn Glu Leu His Ile Pro Val Lys Leu Val Gly Leu Gly Glu Lys Val
    290                 295                 300

Asp Asp Leu Gln Glu Phe Asp Pro Glu Ser Tyr Val Tyr Gly Leu Phe
305                 310                 315                 320

Ser Asp Leu Val Glu Lys Ala Asp Asp
                325

```
<210> SEQ ID NO 9
<211> LENGTH: 118
<212> TYPE: PRT
<213> ORGANISM: Canis familiaris

<400> SEQUENCE: 9
```

Pro Tyr Val Val Thr Phe Cys Gly Val Asn Gly Val Gly Lys Ser Thr

```
  1               5                   10                  15
Asn Leu Ala Lys Ile Ser Phe Trp Leu Leu Glu Asn Gly Phe Ser Val
                20                  25                  30

Leu Ile Ala Ala Cys Asp Thr Phe Arg Ala Gly Ala Val Glu His Val
            35                  40                  45

Arg Thr His Thr Arg Arg Leu Ser Ala Leu His Pro Pro Glu Lys His
        50                  55                  60

Ala Gly Pro Thr Met Val Gln Leu Phe Glu Lys Gly Tyr Gly Lys Asp
65                  70                  75                  80

Ala Ala Gly Ile Ala Met Glu Ala Ile Ala Phe Ala Arg Asn Gln Gly
                85                  90                  95

Phe Asp Val Val Leu Val Asp Thr Ala Gly Arg Met Gln Asp Asn Ala
                100                 105                 110

Pro Leu Met Thr Ala Leu
        115
```

<210> SEQ ID NO 10
<211> LENGTH: 118
<212> TYPE: PRT
<213> ORGANISM: Homo sapiens

<400> SEQUENCE: 10

```
Pro Tyr Val Val Thr Phe Cys Gly Val Asn Gly Val Gly Lys Ser Thr
1               5                   10                  15

Asn Leu Ala Lys Ile Ser Phe Trp Leu Leu Glu Asn Gly Phe Ser Val
                20                  25                  30

Leu Ile Ala Ala Cys Asp Thr Phe Arg Ala Gly Ala Val Glu Gln Leu
            35                  40                  45

Arg Thr His Thr Arg Arg Leu Ser Ala Leu His Pro Pro Glu Lys His
        50                  55                  60

Gly Gly Arg Thr Met Val Gln Leu Phe Glu Lys Gly Tyr Gly Lys Asp
65                  70                  75                  80

Ala Ala Gly Ile Ala Met Glu Ala Ile Ala Phe Ala Arg Asn Gln Gly
                85                  90                  95

Phe Asp Val Val Leu Val Asp Thr Ala Gly Arg Met Gln Asp Asn Ala
                100                 105                 110

Pro Leu Met Thr Ala Leu
        115
```

<210> SEQ ID NO 11
<211> LENGTH: 129
<212> TYPE: PRT
<213> ORGANISM: Saccharomyces cerevisiae

<400> SEQUENCE: 11

```
Pro Tyr Val Phe Ser Ile Val Gly Val Asn Gly Val Gly Lys Ser Thr
1               5                   10                  15

Asn Leu Ser Lys Leu Ala Phe Trp Leu Leu Gln Asn Asn Phe Lys Val
                20                  25                  30

Leu Ile Val Ala Cys Asp Thr Phe Arg Ser Gly Ala Val Glu Gln Leu
            35                  40                  45

Arg Val His Val Glu Asn Leu Ala Gln Leu Met Asp Asp Ser His Val
        50                  55                  60

Arg Gly Ser Lys Asn Lys Arg Gly Lys Thr Gly Asn Asp Tyr Val Glu
65                  70                  75                  80

Leu Phe Glu Ala Gly Tyr Gly Gly Ser Asp Leu Val Thr Lys Ile Ala
```

```
                    85                  90                  95

Lys Gln Ala Ile Lys Tyr Ala Arg Asp Gln Asn Phe Asp Ile Val Leu
                100                 105                 110

Met Asp Thr Ala Gly Arg Arg His Asn Asp Pro Thr Leu Met Ser Pro
        115                 120                 125

Leu

<210> SEQ ID NO 12
<211> LENGTH: 105
<212> TYPE: PRT
<213> ORGANISM: Sulfolobus solfataricus

<400> SEQUENCE: 12

Pro Phe Val Ile Ile Phe Phe Gly Val Asn Gly Val Gly Lys Thr Thr
  1               5                  10                  15

Thr Ile Ala Lys Val Val Asn Met Leu Lys Lys Asn Asn Leu Ser Thr
                 20                  25                  30

Ile Ile Ala Ala Ser Asp Thr Phe Arg Ala Ala Gln Glu Gln Leu
             35                  40                  45

Ala Tyr His Ala Ser Lys Leu Glu Val Gln Leu Ile Arg Gly Lys Tyr
         50                  55                  60

Gly Ala Asp Pro Ala Ser Val Ala Phe Asp Ala Ile Ser Phe Ala Lys
 65                  70                  75                  80

Ser Arg Asn Ile Asp Val Val Leu Ile Asp Thr Ala Gly Arg Met His
                 85                  90                  95

Ile Asp Ser Asp Leu Val Glu Glu Leu
            100                 105

<210> SEQ ID NO 13
<211> LENGTH: 105
<212> TYPE: PRT
<213> ORGANISM: Escherichia coli

<400> SEQUENCE: 13

Pro Phe Val Ile Leu Met Val Gly Val Asn Gly Val Gly Lys Thr Thr
  1               5                  10                  15

Thr Ile Gly Lys Leu Ala Arg Gln Phe Glu Gln Gln Gly Lys Ser Val
                 20                  25                  30

Met Leu Ala Ala Gly Asp Thr Phe Arg Ala Ala Ala Val Glu Gln Leu
             35                  40                  45

Gln Val Trp Gly Gln Arg Asn Asn Ile Pro Val Ile Ala Gln His Thr
         50                  55                  60

Gly Ala Asp Ser Ala Ser Val Ile Phe Asp Ala Ile Gln Ala Ala Lys
 65                  70                  75                  80

Ala Arg Asn Ile Asp Val Leu Ile Ala Asp Thr Ala Gly Arg Leu Gln
                 85                  90                  95

Asn Lys Ser His Leu Met Glu Glu Leu
            100                 105

<210> SEQ ID NO 14
<211> LENGTH: 23
<212> TYPE: PRT
<213> ORGANISM: Canis familiaris

<400> SEQUENCE: 14

Ser Thr Asn Leu Ala Lys Ile Ser Phe Trp Leu Leu Glu Asn Gly Phe
  1               5                  10                  15
```

-continued

Ser Val Leu Ile Ala Ala Cys
            20

<210> SEQ ID NO 15
<211> LENGTH: 23
<212> TYPE: PRT
<213> ORGANISM: Homo sapiens

<400> SEQUENCE: 15

Ser Thr Asn Leu Ala Lys Ile Ser Phe Trp Leu Leu Glu Asn Gly Phe
1               5                   10                  15

Ser Val Leu Ile Ala Ala Cys
            20

<210> SEQ ID NO 16
<211> LENGTH: 23
<212> TYPE: PRT
<213> ORGANISM: Saccharomyces cerevisiae

<400> SEQUENCE: 16

Ser Thr Asn Leu Ser Lys Leu Ala Phe Trp Leu Leu Gln Asn Asn Phe
1               5                   10                  15

Lys Val Leu Ile Val Ala Cys
            20

<210> SEQ ID NO 17
<211> LENGTH: 23
<212> TYPE: PRT
<213> ORGANISM: Sulfolobus solfataricus

<400> SEQUENCE: 17

Thr Thr Thr Ile Ala Lys Val Val Asn Met Leu Lys Lys Asn Asn Leu
1               5                   10                  15

Ser Thr Ile Ile Ala Ala Ser
            20

<210> SEQ ID NO 18
<211> LENGTH: 23
<212> TYPE: PRT
<213> ORGANISM: Escherichia coli

<400> SEQUENCE: 18

Thr Thr Thr Ile Gly Lys Leu Ala Arg Gln Phe Glu Gln Gln Gly Lys
1               5                   10                  15

Ser Val Met Leu Ala Ala Gly
            20

<210> SEQ ID NO 19
<211> LENGTH: 23
<212> TYPE: PRT
<213> ORGANISM: Bacillus subtilis

<400> SEQUENCE: 19

Thr Thr Thr Ile Gly Lys Leu Ala His Lys Met Lys Gln Glu Gly Lys
1               5                   10                  15

Ser Val Val Leu Ala Ala Gly
            20

<210> SEQ ID NO 20
<211> LENGTH: 4370
<212> TYPE: DNA
<213> ORGANISM: Bacillus subtilis

<400> SEQUENCE: 20

```
ctgcaggaac ggcatgatat ttctgcgcgt aaagccgcat gtgaaacgga atttgcccga        60
attgagcagg agattcacag tcaagtcggt gcatatcgtg atatgcagac aaaatatgag       120
cagaaaaagc gccaatacga aaaaaatgaa tccgctctgt atcaggcata ccaatacgtt       180
cagcaagcga gatcaaaaaa ggacatgctt gagacgatgc agggagattt ctccggcttt       240
tatcaaggtg ttaaagaagt gctgaaagcg aaagagcgcc ttggcggaat tcgcggagcg       300
gttcttgagc tgatttctac agaacagaag tatgaaacgg ccattgaaat agcgctcggc       360
gcttctgctc aacacgtcgt gaccgacgat gaacaatctg cccgcaaagc gattcaatat       420
ttaaagcaga attccttcgg ccgggcgacg tttctgcctc tttctgttat tagagaccgc       480
cagcttcaaa gccgtgacgc ggaaacagcc gcccggcatt catcatttct cggggttgcc       540
agtgaacttg tcacatttga tcctgcgtat cgaagcgtca tccagaatct tcttggaacc       600
gttctgatca cagaggactt aaagggtgca acgagcttg cgaagcttct cgggcaccgg       660
taccgcatcg taacccttga gggagatgtt gtgaaccccg gtggttcaat gacgggcggc       720
gcggttaaaa agaaaaataa ctccctcctt ggaagaagcc gggagctaga agatgtgacg       780
aaacggctcg ctgaaatgga agagaaaacg gcactgcttg aacaagaggt caaaaccctt       840
aagcactcca ttcaggatat ggagaaaaaa ctggctgact aagagaaac cggggaaggc       900
ttaaggttaa agcagcagga tgtgaaaggc cagctgtacg aacttcaagt tgccgagaaa       960
aatatcaata cccatttaga gctctatgat caagaaaaat ctgctctgtc agaaagcgat      1020
gaagagagaa aagtgcgcaa acgcaagctt gaagaagagc tctctgccgt atctgaaaag      1080
atgaaacagc ttgaagagga catagacaga ctgacaaaac aaaaacaaac gcaatcctca      1140
acgaaagagt ctctctccaa cgagctgact gagctgaaga tcgcagcggc caaaaaagag      1200
caggcttgcg aggggggaaga ggacaacctt gccagattaa agaaagagct cactgaaaca      1260
gagcttgcgt taaagaagc aaaagaagac ttaagcttct taacgtcaga gatgtcatct      1320
agcaccagcg gcgaagaaaa gctggaagaa gcagcaaaac ataaattgaa tgacaaaacg      1380
aaaacgatcg aactgattgc attaaggcgc gatcagcgca tcaagcttca gcatgggctt      1440
gatacgtatg agcgtgagct gaagaaatg aaacgcctgt ataaacaaaa acaacgctc      1500
ttaaaagacg aagaagtcaa acttggacga atggaagtcg agcttgataa tttactccaa      1560
tacttacggg aggaatacag cttgtccttt gaggggggcaa aagagaaata tcagcttgaa      1620
actgatccag aggaagccag aaagcgcgtg aagctgatta aactcgcaat tgaagagctg      1680
ggtaccgtga acctcggaag catagatgag tttgagaggg tcaacgaacg gtacaagttt      1740
ctgtcggaac aaaaagaaga tttaacagaa gcgaaaaata ccttgttcca agtgattgaa      1800
gaaatggatg aagaaatgac gaagcgcttt aacgacacat tcgtccaaat ccgctcacac      1860
tttgatcaag ttttccgctc cttattcgga ggagggcgag ctgaactgag gctcaccgat      1920
cctaacgact cctcatcagg atcgagatta tcgctcagcc gccggggaaa aactccaaac      1980
tttaacctcc tgtcaggcgg agagcgtgcg cttactgcta tagcgctctt attctcaatc      2040
ctaaaggttc gtccagtgcc gttttgcgcc cttgacgaag tagaggctgc gctcgacgaa      2100
gcgaatgtgt tccgatttgc gcagtactta aaaaaataca gcagcgatac tcagtttatt      2160
gtaattaccc acagaaaagg aacgatggag gaagcggatg tgctttatgg cgtaaccatg      2220
caggaatccg gtgtttccaa ggtaatttca gttaagctgg aagaaacaaa agaattcgtt      2280
cagtaacgag gaaagaggtt aaaagatgag cttttttaaa aaattaaaag agaaaatcac      2340
```

```
aaaacagaca gattccgtat ctgaaaagtt taaggatggc cttgaaaaaa caagaaactc    2400
ctttcaaaac aaagtgaatg atcttgtatc ccgttaccgt aaagtggatg aggatttctt    2460
cgaagagctt gaagaggttc ttatcagcgc ggatgtcggt tttacaaccg ttatggaatt    2520
aatagatgag ctgaaaaaag aagtcaaacg cagaaatatt caagatccaa aggaagtcaa    2580
gtcagtgatt tctgagaaac tggtcgagat ttataacagc ggagatgagc aaatttcaga    2640
actgaacatc caggatgggc gtttaaacgt aatccttctg gtaggtgtaa acggcgtcgg    2700
gaaaacaaca acgatcggaa agcttgctca taaaatgaaa caagaaggaa aatctgttgt    2760
acttgccgcc ggagacactt ttagagcggg agccattgaa cagctggaag tatggggaga    2820
gcgtacagga gtgcctgtca ttaagcagac ggcaggaagc gatccggcgg ctgtcatcta    2880
cgatgctgtt catgctgcga aagcaagaaa tgccgatgta ttaatttgtg atacggcagg    2940
gcgtctccaa aacaaagtaa atctcatgaa agagcttgaa aaagtaaaac gtgttatcga    3000
aagagaagtt cctgaagctc cgcatgaggt gctgcttgcc cttgatgcca cgaccggcca    3060
aaatgcaatg gctcaggcaa aagaattctc taaagcaaca aatgttaccg gcattgcttt    3120
aacgaagctt gacggtacgg caaaaggcgg tatcgtcctt gcgattcgca acgagcttca    3180
catcccggtt aaactagtcg gtttaggaga aaaagttgat gaccttcagg aatttgatcc    3240
agaatcctat gtgtacggac tcttttcaga tttagtggaa aaagccgacg attaagaaaa    3300 aggcccccaac atcttggggc cttttctttt tttatcttct tacttgatag gcgaaatgat    3360
aaaggctgtt atcagtggat accagtcttg actcaccaga aaaaactctg aatgggatga    3420
tgtcatagta atgaacggaa acagatgtgt aatacgtata gtaaccagca gctggcccca    3480
aatacattgg aacctcaaat gttccgtttg catcagtcgt tcctgaagca gtttgtgttg    3540
tgtttccgac cttcgtgtcc gcttcaaatc ttacgggcgc gtttggcact ggctgtccgt    3600
tttggtcgag taatttgccg cttactgtaa tattgtactt gactcgcaat attgaccttg    3660
tccgtaattg attttaccgt ataccctcc atctgtgctg atatttgtga ttgaggcctt    3720
ataaggtgcc tcagcagcgt ctgcttgctg tgccgggaaa cctattgtaa acagggctgc    3780
cagacataac ataaacaata aaccgatttt tttcataaaa atcctcctta aaatagggtt    3840
catatacaat atcggaataa attggatgat atttagcgta ttttggaaaa gttaatcgcc    3900
gctttgacaa gataaaaact tgacagtgtc attaaaaccg tgtaaactaa gttatcgtaa    3960
agggatttga cttaacaagg ggagagctca aatgtcactc gaaaagacaa gcagaatgaa    4020
ttatctgttt gatttttatc agccgttgtt gacgtcaaaa cagaagagct atatgtcgct    4080
ttattatttg gacgatttct ccctaggcga aatagccgaa gaatatgagg tttcaagaca    4140
agctgtttat gataacatca aacgaacaga agcaatgctt gaacaatatg aagaaaagct    4200
gctccttttg aaaaagtttc aggagcgtaa agagatgttt aataagctga aggagcttgc    4260
ttccggttca aaagaagagg aagaaattac agctctgatt gaagcgcttg agaaattaga    4320
ttaggaggcg gcaaactatg gcatctgaag gattagccga ccgactgcag               4370
```